US008439925B2

(12) United States Patent
Marino et al.

(10) Patent No.: US 8,439,925 B2
(45) Date of Patent: May 14, 2013

(54) TRANSILIAC-TRANSSACRAL METHOD OF PERFORMING LUMBAR SPINAL INTERVENTIONS

(75) Inventors: James F. Marino, La Jolla, CA (US); Jamil Elbanna, San Diego, CA (US)

(73) Assignee: Trinity Orthopedics, LLC, San Diego, CA (US)

( * ) Notice: Subject to any disclaimer, the term of this patent is extended or adjusted under 35 U.S.C. 154(b) by 153 days.

(21) Appl. No.: 12/778,057

(22) Filed: May 11, 2010

(65) Prior Publication Data
US 2011/0009869 A1    Jan. 13, 2011

Related U.S. Application Data

(60) Provisional application No. 61/177,055, filed on May 11, 2009.

(51) Int. Cl.
*A61B 17/56*     (2006.01)

(52) U.S. Cl.
USPC ............. 606/87; 606/96; 606/98; 606/102; 606/104

(58) Field of Classification Search ............... 606/86 R, 606/87, 80, 98, 96, 102, 104
See application file for complete search history.

(56) References Cited

U.S. PATENT DOCUMENTS

| | | | |
|---|---|---|---|
| 5,242,444 A | 9/1993 | MacMillan | |
| 5,334,205 A * | 8/1994 | Cain | ................ 606/96 |
| 5,423,826 A | 6/1995 | Coates et al. | |
| 5,569,248 A | 10/1996 | Mathews | |
| 6,080,157 A | 6/2000 | Cathro et al. | |
| 6,224,603 B1 | 5/2001 | Marino | |
| 6,358,254 B1 | 3/2002 | Anderson | |
| 6,485,518 B1 | 11/2002 | Cornwall et al. | |
| 6,520,967 B1 | 2/2003 | Cauthen | |
| 6,575,899 B1 | 6/2003 | Foley et al. | |
| 6,814,737 B2 | 11/2004 | Cauthen | |
| 2003/0004517 A1 | 1/2003 | Anderson | |
| 2003/0191474 A1 | 10/2003 | Cragg et al. | |
| 2003/0199871 A1 | 10/2003 | Foley et al. | |

(Continued)

FOREIGN PATENT DOCUMENTS

| | | |
|---|---|---|
| WO | 00/48521 | 8/2000 |
| WO | 00/62684 | 10/2000 |

(Continued)

OTHER PUBLICATIONS

MacMillan, MD, et al., (1996) "Percutaneous Lumbosacral Fixation and Fusion—Anatomic Study and Two-Year Experience with a New Method", Percutaneous Spine Techniques, *Neurosurgery Clinics of North America*, vol. 7, No. 1, pp. 99-106.

*Primary Examiner* — Todd Manahan
*Assistant Examiner* — Marcela I Shirsat
(74) *Attorney, Agent, or Firm* — Fred C. Hernandez; Mintz Levin Cohn Ferris Glovsky and Popeo, P.C.

(57) ABSTRACT

This disclosure is directed to minimally-invasive devices, methods and systems for treating vertebral diseases and injuries using multiple therapeutic procedures through small access portals of sufficient dimension that minimize trauma to the patient. More particularly, disclosed herein are devices, methods and systems for an intraosseous transiliac-transsacral surgical approach through the iliac ala and sacral ala that can be used for a variety of surgical procedures within the lumbar spine.

17 Claims, 23 Drawing Sheets

U.S. PATENT DOCUMENTS

| | | |
|---|---|---|
| 2003/0212400 A1 | 11/2003 | Bloemer et al. |
| 2004/0092933 A1 | 5/2004 | Shaolian et al. |
| 2005/0125066 A1 | 6/2005 | McAfee |
| 2005/0187556 A1 | 8/2005 | Stack et al. |
| 2005/0283246 A1 | 12/2005 | Cauthen et al. |
| 2006/0115055 A1 | 6/2006 | Marino |
| 2007/0127626 A1 | 6/2007 | Marino |
| 2007/0162044 A1 | 7/2007 | Marino |
| 2011/0118841 A1* | 5/2011 | Reiley .................. 623/17.11 |

FOREIGN PATENT DOCUMENTS

| | | |
|---|---|---|
| WO | 01/41681 | 6/2001 |
| WO | 2006/116606 | 11/2006 |
| WO | 2007/062132 | 5/2007 |
| WO | 2007/062133 | 5/2007 |

* cited by examiner

TRANSILIAC-TRANSSACRAL METHOD OF PERFORMING LUMBAR SPINAL INTERVENTIONS

This application claims priority of U.S. Provisional Patent Application Ser. No. 61/177,055, entitled "Transiliac-transsacral Method of Performing Lumbar Spinal Interventions," filed May 11, 2009. Priority of the filing date of May 11, 2009 is hereby claimed and the disclosure of the provisional patent application is hereby incorporated by reference in its entirety.

BACKGROUND

This disclosure relates generally to spinal surgery involving the lower lumbar vertebrae. More specifically, this disclosure relates to devices and methods for an intraosseous surgical approach through the sacral ala to the lumbar spine for a variety of interventions including intervertebral fixation, disc excision and/or ablation.

A significant number of adults have had an episode of back pain or suffer chronic back pain emanating from a region of the spinal column. A number of spinal disorders are caused by traumatic spinal injuries, disease processes, aging processes, and congenital abnormalities that cause pain, reduce the flexibility of the spine, decrease the load bearing capability of the spine, shorten the length of the spine, and/or distort the normal curvature of the spine. Many people suffering back pain resort to surgical intervention to alleviate their pain.

Disc degeneration can contribute to back pain. With age, the nucleus pulposus of the intervertebral discs tends to become less fluid and more viscous. Dehydration of the intervertebral disc and other degenerative effects can cause severe pain. Annular fissures also may be associated with a herniation or rupture of the annulus causing the nucleus to bulge outward or extrude out through the fissure and impinge upon the spinal column or nerves (a "ruptured" or "slipped" disc).

In addition to spinal deformities that occur over several motion segments, spondylolisthesis (forward displacement of one vertebra over another, usually in the lumbar or cervical spine) is associated with significant axial and/or radicular pain. Patients who suffer from such conditions can experience diminished ability to bear loads, loss of mobility, extreme and debilitating pain, and oftentimes suffer neurological deficit in nerve function.

Failure of conservative therapies of spinal pain such as bed rest, pain and muscle relaxant medication, physical therapy or steroid injection often leads patients to seek spinal surgical intervention. Many surgical techniques, instruments and spinal disc implants have been described that are intended to provide less invasive, percutaneous, or minimally-invasive access to a degenerated intervertebral spinal disc. Instruments are introduced through the annulus for performing a discectomy and implanting bone growth materials or biomaterials or spinal disc implants within the annulus. One or more annular incisions are made into the disc to receive spinal disc implants or bone growth material to promote fusion, or to receive a pre-formed, artificial, functional disc replacement implant.

Extensive perineural dissection and bone preparation can be necessary for some of these techniques. In addition, the disruption of annular or periannular structures can result in loss of stability or nerve injury. As a result, the spinal column can be further weakened and/or result in surgery-induced pain syndromes. One technique for spinal fixation includes the immobilization of the spine by the use of spine rods of various configurations that run generally parallel to the long axis of the spine. Typically, the posterior surface of the spine is isolated and bone screws are first fastened to the pedicles of the appropriate vertebrae or to the sacrum such that they act as anchor points for the spine rods. The bone screws are generally placed two per vertebra, one at each pedicle on either side of the spinous process.

Persistent low back pain is often attributed to degeneration of the disc connecting L5 and S1. Highly invasive techniques have been proposed for the treatment of such degeneration through surgical fixation and fusion of the lower lumbar vertebrae. For example, one technique involves a posterior approach for the removal of the painful disc and fusion of the adjacent vertebrae to relieve the low back pain. This method commonly requires extensive surgical dissection, including stripping of the paraspinal musculature and nerve retraction. Another technique is anterior lumbar fusion in which the spine is approached through the abdomen, and has associated requirements for the mobilization and/or protection of peritoneal and retroperitoneal structures. Other surgeries are designed to fuse and stabilize the intervertebral segment through a lateral approach, which commonly entails dissection through the psoas muscle and its invested lumbosacral nerves.

Another surgical approach involves access of the superior disc space through the sacral pedicles. This technique also suffers from several disadvantages. For example, approaching the L5-S1 disc space through the S1 pedicles have proven relatively difficult and impractical. The techniques are very demanding and prior surgical navigation techniques have been relatively unreliable in providing the precise navigation required to approach the L5-S1 disc space via the S1 pedicles. Due to the relative position of the S1 pedicles and the L5-S1 disc space, this approach suffers from limitations in disc space access and manipulation of surgical tools within. The approach weakens, violates and/or removes bone from the S1 pedicle(s) in a manner that could potentially compromise the sacral pedicle fixation.

SUMMARY

There remains a need for minimally-invasive surgical approaches for performing therapeutic procedures in the spine. In particular, there is a need for minimally-invasive access to L5-S1 region of the spine for interventions such as disc excision and interbody implant insertion.

In an embodiment disclosed is a method of accessing the lumbosacral region of a patient including percutaneously forming a bony pathway by inserting bone penetration instrumentation through a portion of an iliac ala, sacroiliac joint, and sacral ala to a region of a L5-S1 disc space. In an embodiment, the bony pathway can align generally parallel to a coronal plane of the L5-S1 disc space. The bony pathway can approach the L5-S1 disc space along a coronal plane of the L5-S1 disc space at an angle that is between about 5 and 40 degrees relative to an axial plane of the L5-S1 disc. The bony pathway can approach the L5-S1 disc space along a coronal plane of the L5-S1 disc space at an angle that is between about 5 and 20 degrees relative to an axial plane of the L5-S1 disc. The bony pathway can approach the L5-S1 disc space along a coronal plane of the L5-S1 disc space at an angle that is generally parallel to an axial plane of the L5-S1 disc.

The method can further include percutaneously placing a guide instrument in a sacral pedicle. The guide instrument can have a longitudinal axis that aligns with an axial plane of the L5-S1 disc space from a generally posterior to posterior-lateral aspect of the sacral pedicle to a generally anterior or anterior-medial aspect of the sacral pedicle. The method can further include attaching to the guide instrument a curvilinear frame having a port adjustably offset at an angle from the longitudinal axis of the guide instrument. The curvilinear frame can provide an arcuate track along which the port provides a directed surgical path intersecting the longitudinal axis of the guide instrument at a location anterior to the sacral pedicle.

The method can further include adjusting the port along the curvilinear frame such that the angle of the port relative to the longitudinal axis of the guide instrument is between about 50 and 100 degrees. Inserting the bone penetration instrumentation through the port can direct a distal end of the bone penetration instrumentation to contact the iliac ala. The method can further include performing disc excision in the L5-S1 disc space. The bone penetration instrumentation can extend through the L5-S1 disc space to contact the vertebral body of L5 vertebra. The method can further include performing endplate decortication of the L5 vertebra. The method can further include inserting a lumbosacral transfixation construct through the bony pathway. The method can further include performing an intervention including intervertebral fixation, intervertebral distraction, intervertebral fusion, disc excision, arthroplasty and nucleoplasty.

The method can further include percutaneously forming a bony pathway by inserting bone penetration instrumentation through a contra-lateral iliac ala, sacroiliac joint, and sacral ala to the region of the L5-S1 disc space. The contra-lateral bony pathway can provide bilateral access to the region of the L5-S1 disc space.

DETAILED DESCRIPTION

Disclosed are methods and devices for accessing and treating the spine while minimizing trauma to surrounding tissue. The present disclosure relates generally to spinal surgery, particularly methods and systems for forming one or more intraosseous access bores in a minimally-invasive, low-trauma manner and providing a therapy to the spine employing at least a portion of the intraosseous bore. The method disclosed herein is directed generally to disc access using a surgical path that courses through the iliac and sacral alae in a plane that approximates the plane of the intervertebral disc to be treated and associated endplates. The pathway can approach the intervertebral disc of L5-S1 on an axis that is along the coronal plane of the L5-S1 disc space and between about 5-40 degrees relative to a plane that approximates the axial plane of the L5-S1 disc. In an embodiment, the pathway approaches the intervertebral disc of L5-S1 on an axis that is along the coronal plane of the L5-S1 disc space and generally parallel relative to a plane that approximates the axial plane of the L5-S1 disc. The surgical approach allows for improved disc and endplate access for associated interventions (e.g. disc excision and endplate decortication) and permits the manipulation and introduction of larger elements.

Figure 1A:
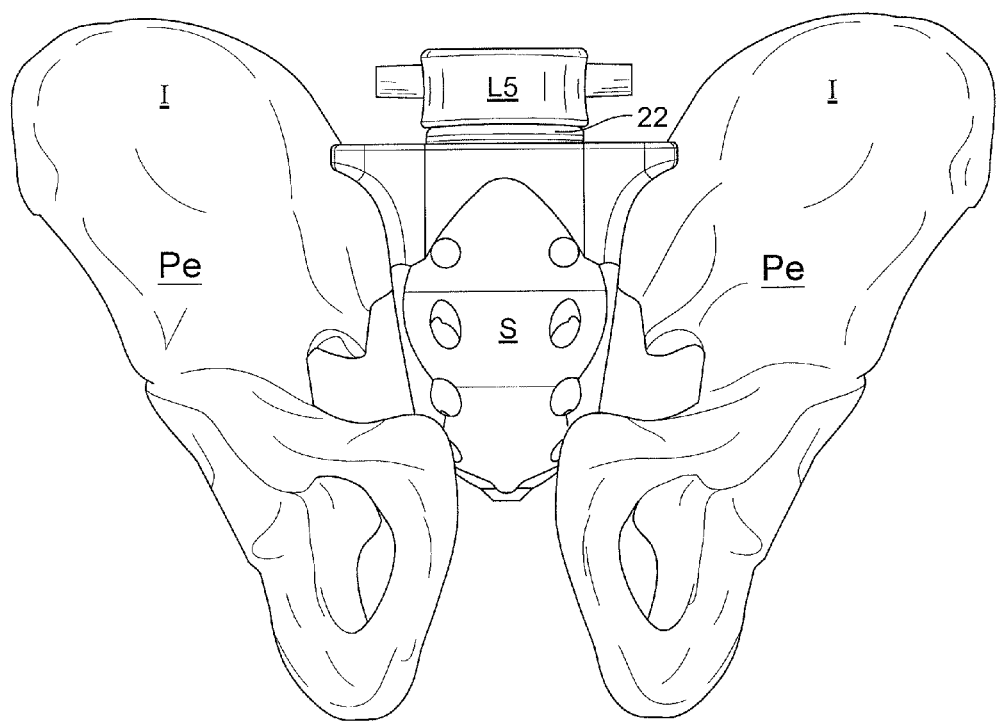
FIG. 1A is a simplified, anterior view of the lumbosacral region of the spine including the pelvis.
Figure 1B:
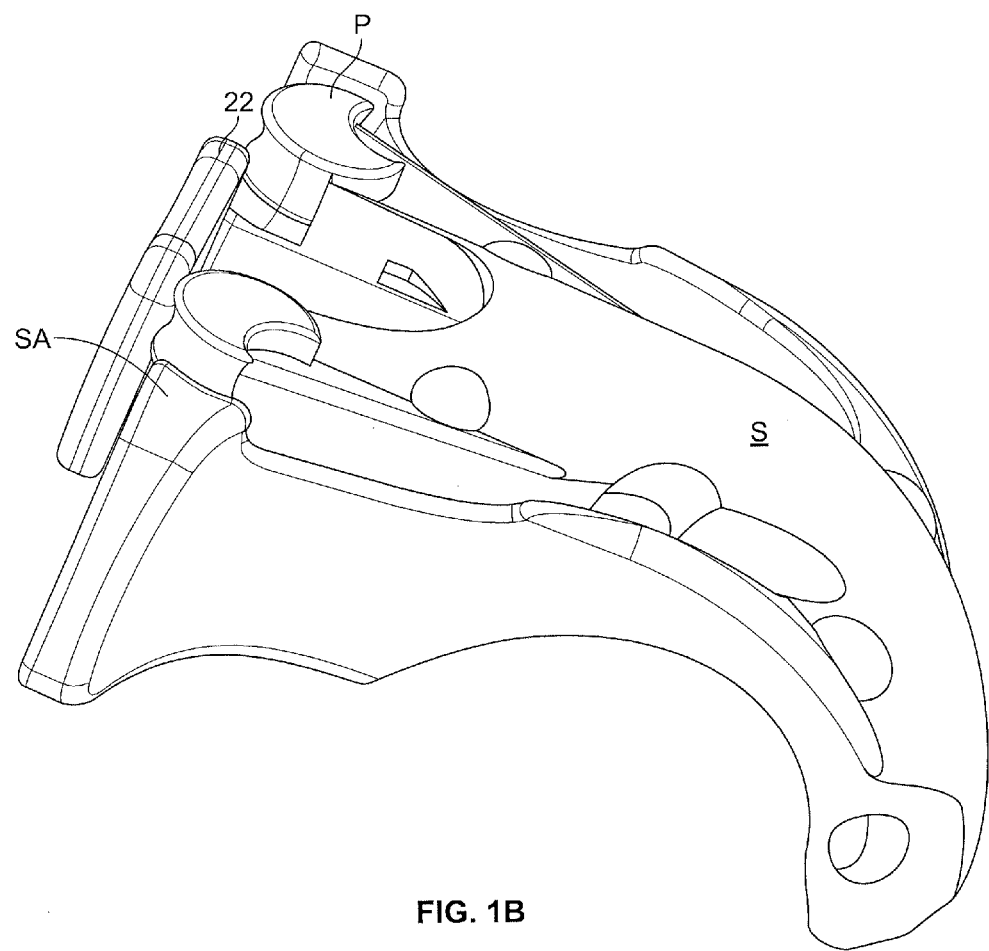
FIG. 1B is a simplified, isometric view of the sacrum and L5-S1 disc.

FIG. 1A is a simplified anterior view of the lumbosacral region of the spine including the fifth lumbar vertebra (L5), the sacrum (S) and the pelvis (Pe). FIG. 1B is a simplified, isometric view of the sacrum and L5-S1 disc. Due to disc degeneration, expulsion, annulus tears, or other conditions, the cauda equina and lumbosacral nerve roots that pass through the central canal in the L5 vertebra can become compressed causing patient discomfort. A variety of surgical interventions that modify or alter the native architecture of the L5-S1 intervertebral disc, and/or its associated adjacent vertebrae are utilized to address various symptomatic conditions. FIGS. 2-7B present various methods and systems for accessing the L5-S1 disc space to perform a surgical procedure.

It can be desirable to access the lumbar disc space in order to decompress nerves by removing herniated or prolapsed discs. Nuclear replacement or disc replacement procedures have been proposed and performed to restore disc function. In addition to disc excision therapeutic modification and/or replacement techniques, lumbosacral fusion can be performed using a transiliac-transsacral approach as described herein. In an embodiment, access to the L5-S1 disc space or lumbar vertebra L5 can be achieved via a channel formed in a sacral ala to be discussed in more detail below.

Figure 1C:
FIG. 1C is a simplified, dorsal view of the sacrum.

The sacrum (S) shown best in FIG. 1C is a large, triangular bone, situated in the lower part of the vertebral column and at the upper and back part of the pelvic cavity, where it is positioned like a wedge between the two hip bones. Its upper part or base of the sacrum S articulates with the last lumbar vertebra (L5). The apex of the sacrum (S) articulates with the coccyx (C) and on either side it articulates with the ilium (I) or top portion of the pelvis (Pe) (shown in FIG. 1A). The sacrum (S) is curved upon itself and positioned very obliquely, its base projecting forward and forming the prominent sacrovertebral angle. When articulated with L5 the central part of the sacrum (S) is projected backward so as to give increased capacity to the pelvic cavity.

The sacral alae (SA) are the "wings" of the sacrum (S) and are an important part of the connection between the sacrum (S) and pelvis (Pe). The sacroiliac joints occur where the sacral ala (SA) join with the ilium (I). These transmit the loads of the spine to the pelvis and thus to the lower extremities. The sacroiliac joint is an extremely stable structure because of its bony configuration and ligamentous support and is among the strongest joints in the human body (Porterfield, J A, DeRosa, C. *Mechanical Low Back Pain: Perspectives in Functional Anatomy.* Philadelphia, Pa.: W.B. Saunder's Co.; 1976).

Figure 1D:
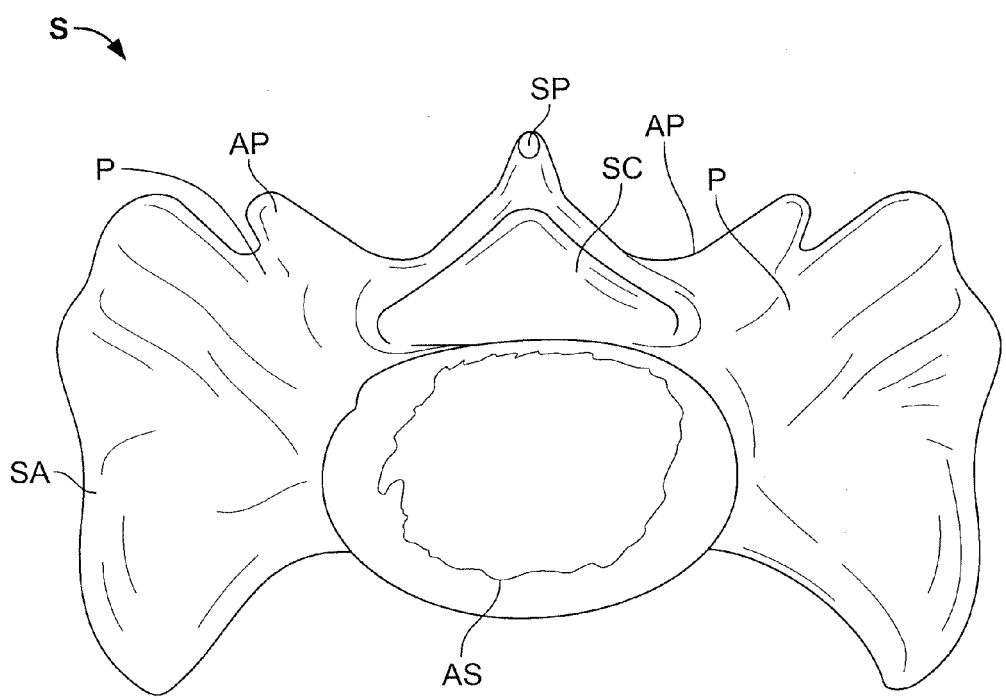
FIG. 1D is a simplified, transverse cephalad axial plane view of the sacrum.

FIG. 1D shows the articular processes (AP) of the sacrum (S), which are large and oval in shape. The articular process facets (F, see FIG. 1C) are concave from side to side, look backward and medial-ward, and articulate with the facets on the inferior processes of the L5 vertebra. FIG. 1D also shows the base of the sacrum (S), which is broad and expanded, is directed upward and forward. In the middle is a large oval articular surface (AS), the superior surface of the body of the sacrum is connected with the inferior surface of the body of L5 vertebra by an intervening fibrocartilage structure, or intervertebral disc 22. Behind this is the triangular orifice of the sacral canal (SC), which is completed by the laminae and spinous process (SP) of the sacrum (S). The superior articular processes (AP) project from it on either side. The articular processes (AP) are oval, concave, directed backward and medial-ward, like the superior articular processes of a lumbar vertebra. They are attached to the body of the sacrum (S) and to the sacral alae (SA) by short thick pedicles (P). On the upper surface of each pedicle (P) is a vertebral notch, which forms the lower part of the foramen between L5 vertebra and the S1.

FIGS. 2 to 7B illustrate methods and devices for forming an intraosseous channel according to various embodiments. A transiliac-transsacral channel can be created through the iliac and sacral alae (IA, SA) forming a working channel that approaches the plane of the disc being treated. Steep angles in the coronal plane can be avoided by using the disclosed methods and devices. The transiliac-transsacral working channel can enable access, for example to the disc space, lumbar vertebrae, vertebral endplate, neuroforamina, epidural space, lateral recess or the like. Because the transiliac-transsacral working channel can approximate the intervertebral disc plane, it is likely to facilitate thorough disc access (e.g. for resection) as well as permit the manipulation and introduction of relatively long tools and implant elements (e.g. intervertebral implants). The transiliac-transsacral working channel can be used for a number of procedures such as disc resection, excision, endplate decortication, vertebral reduction or compression, delivery of material etc. The transiliac-transsacral working channel can also be used for insertion of lumbosacral transfixation constructs and subsequent pedicle screw fixation through the sacral ala, for example. Methods described herein use a common entry for a variety of procedures, for example intervertebral fixation of the L5-S1 vertebra as well as excision, ablation resection, shaving, shearing, cutting or removing of the intervertebral disc material, vertebral reduction or compression, and/or disc or nuclear arthroplasty.

A guide can be employed by placing a pin through a normal entry path in the sacral pedicle(s) generally along the axis of the L5-S1 disc space from a generally posterior or posterior-lateral aspect to a generally anterior or anterior-medial aspect of the S1 pedicle, into and/or through the sacral body. Alternatively, the pin can enter the L5-S1 foramen or the juncture of the foramen and the postero-lateral annulus (within or adjacent to the lateral recess of the spinal canal) thus allowing access to the lumbosacral foramen and lateral recess. The pathway in the sacral pedicle(s) can be used for the purpose of placing a surgical guide for stabilization and anatomic reference. The transiliac-transsacral surgical pathway does not course through the sacral pedicle(s). It should also be appreciated that insertion of bone penetrating instruments described herein can be inserted unilaterally or bilaterally and can employ free-hand techniques or use surgical guides or surgical navigation tools (e.g. image intensifier, MRI or CT scan based technology).

Figure 2:
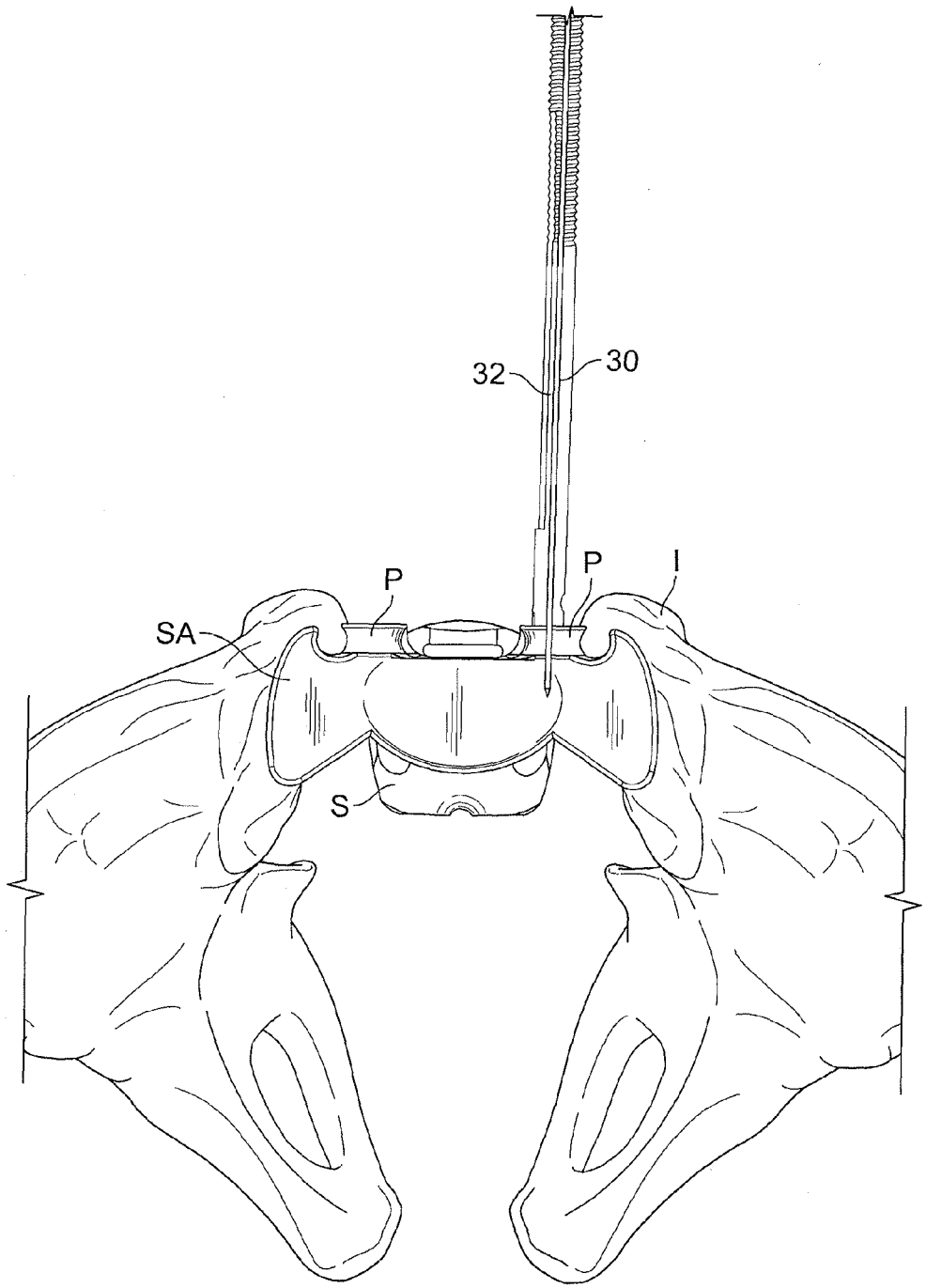
FIG. 2 is a simplified, transverse cephalad view of the sacrum including a guide pin and support sleeve, the guide pin being inserted into a sacral pedicle according to various embodiments.

FIG. 2 is a simplified transverse cephalad view of the sacrum including a guide pin 30 and support sleeve 32 according to various embodiments. In one embodiment, the guide pin 30 can be inserted at a posterior, lateral angle from the coronal view and nearly parallel to the L5-S1 disc plane from the sagittal view. The guide pin 30 can extend into the S1 pedicle (P). In an additional embodiment a support sleeve 32 can be inserted over the guide pin 30. The support sleeve 30 can be a thin-walled cannula in an embodiment of the device. In an embodiment, the anterior cross-sectional area of the intraosseous channel in the S1 pedicle (P) overlaps, is contiguous with or confluent with at least a portion of the transiliac-transsacral ala channel, initially defined by guide pin 30 within the sacral ala (SA), as described in more detail below. It should be appreciated that the surgical guide placed within the sacral pedicle(s) is used for stabilization and anatomic reference. Although the guide is placed in the sacral pedicle(s), the transiliac-transsacral path does not course through the sacral pedicle(s) as described in more detail below.

Figure 3A:
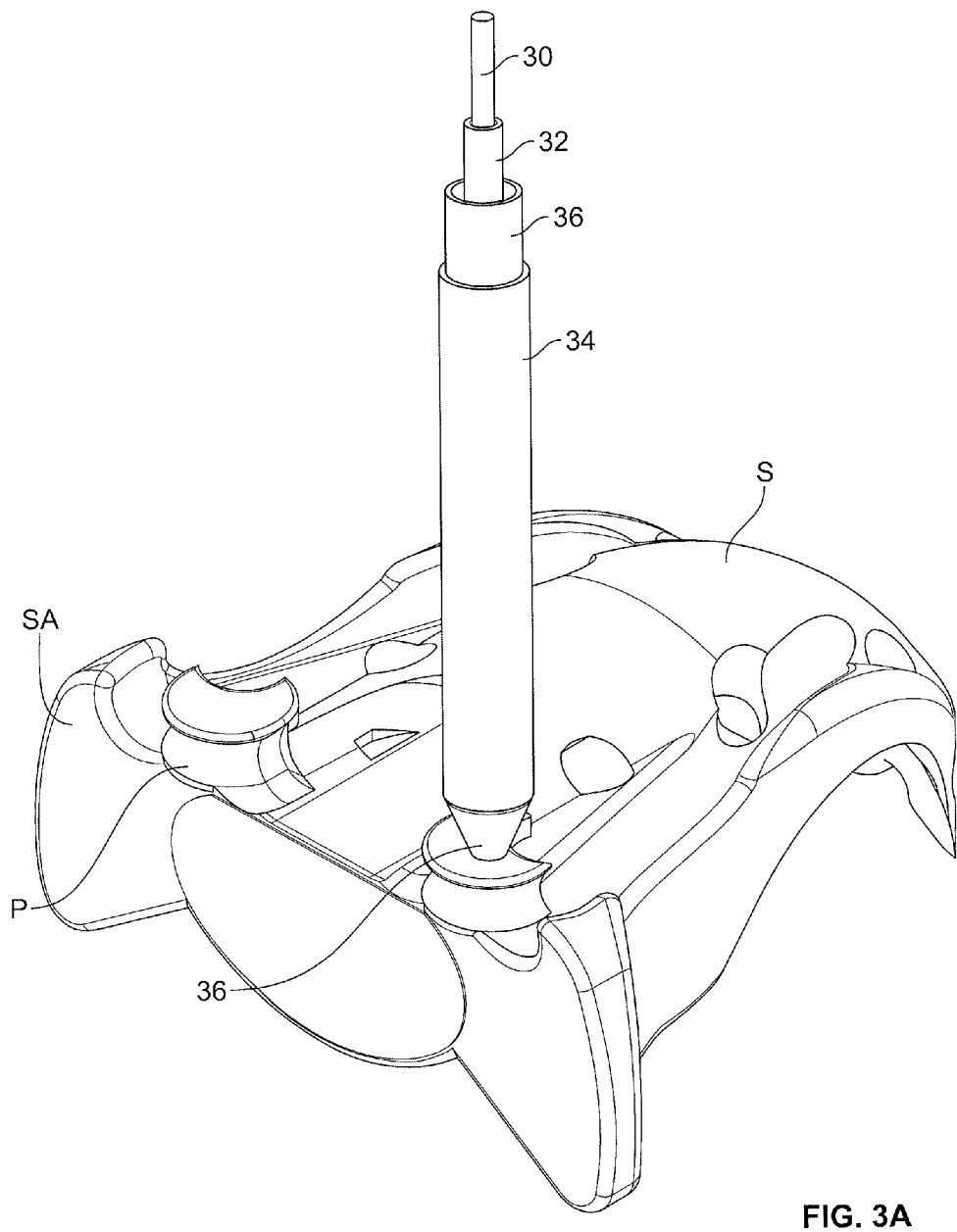
FIG. 3A is a simplified isometric view of the lumbosacral region of the spine shown in FIG. 2 further including an obturator and cannula inserted over the guide pin and support sleeve, the obturator being advanced toward a sacral pedicle to create a soft tissue pathway to the sacral pedicle according to various embodiments.
Figure 3B:
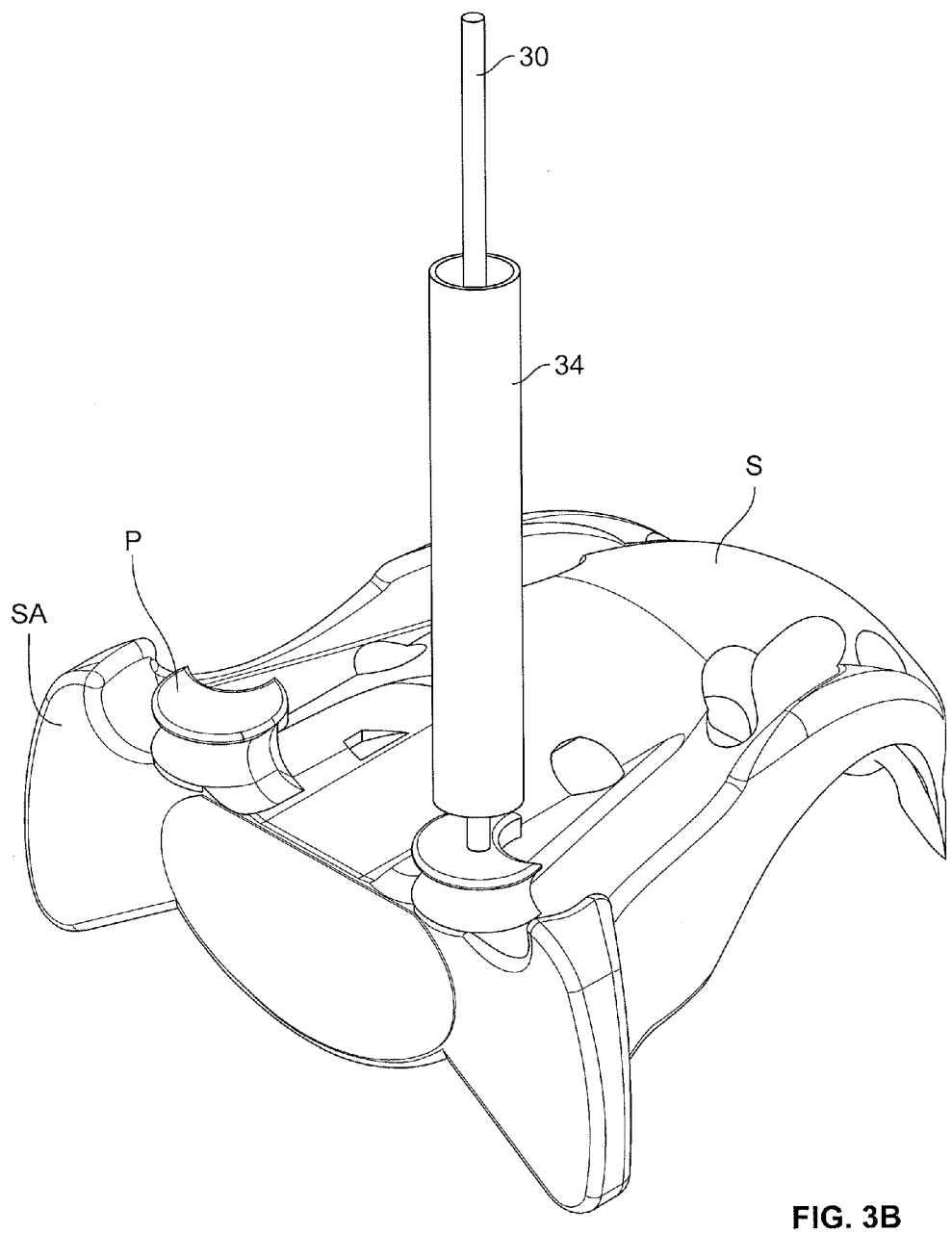
FIG. 3B is a simplified isometric view of the lumbosacral region of the spine where the obturator and guide sleeve have been removed leaving the guide pin inserted into the sacral pedicle with the cannula over the guide pin according to various embodiments.
Figure 3C:
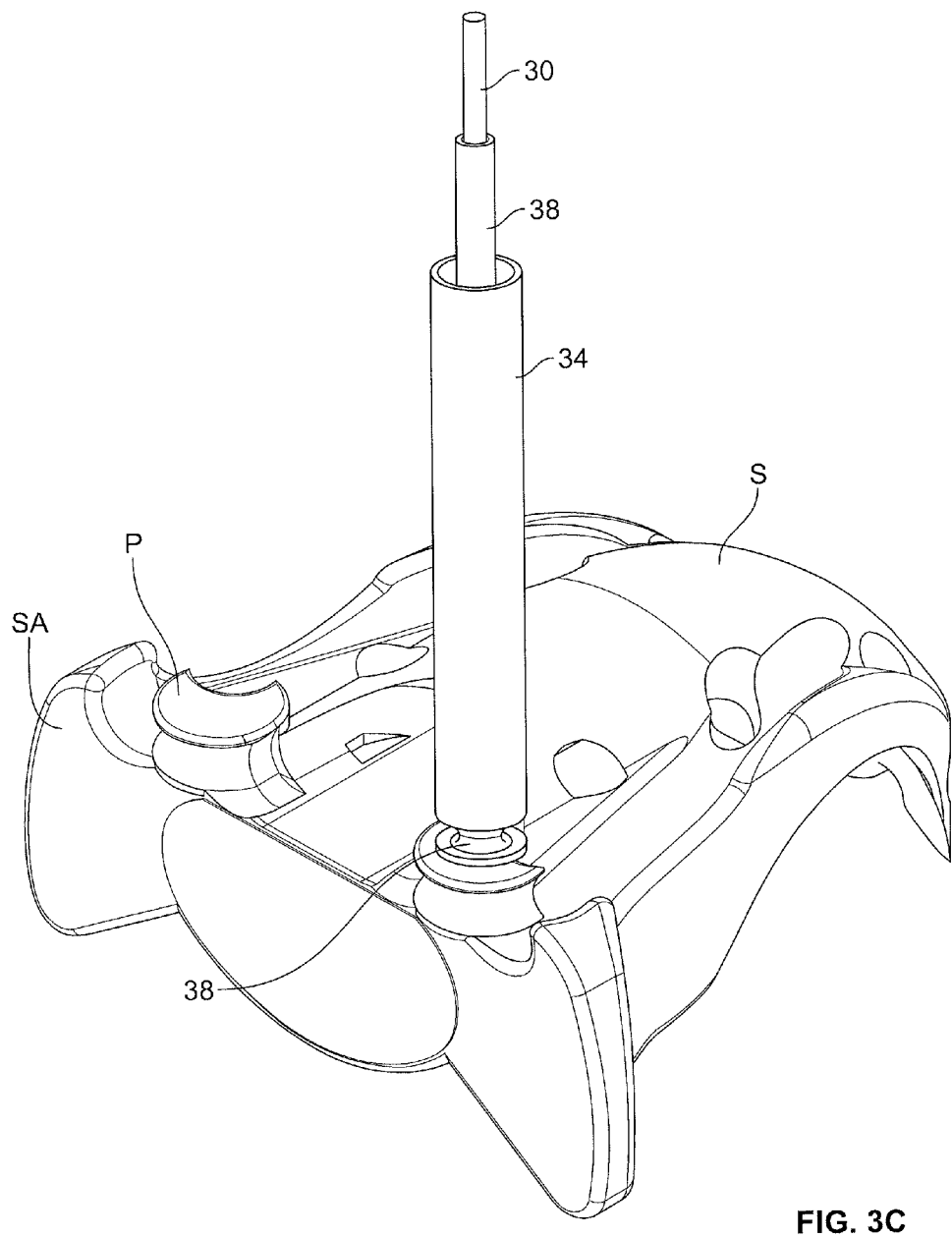
FIG. 3C is a simplified isometric view of the lumbosacral region of the spine shown in FIG. 3B further including a cannulated reamer inserted over the guide pin and within the cannula, the reamer being operatively advanced into the sacral pedicle to form a bore in the sacral pedicle according to various embodiments.

FIG. 3A is a simplified isometric view of the L5-S1 region shown in FIG. 2 further including an obturator 36 and cannula 34 inserted over the guide pin 30 and support sleeve 32. In an embodiment the obturator 36 can be advanced toward the S1 pedicle (P) to create a soft tissue pathway to the L5-S1 disc space. FIG. 3B is a simplified isometric view of the L5-S1 region where the obturator 36 and support sleeve 32 have been removed leaving the guide pin 30 inserted into the 51 pedicle (P) with the cannula 34 over the guide pin 30. FIG. 3C is a simplified isometric view of the L5-S1 region shown in FIG. 3B further including a cannulated reamer 38 inserted over the guide pin 30 and within the cannula 34. In an embodiment, the reamer 38 can be operatively advanced into the S1 pedicle (P) to form a bore in the S1 pedicle (P). In an embodiment the reamer 38 can have about a 4 mm-8 mm diameter. In this embodiment, the reamer 38 can be used to form an approximately 10 mm deep and 6.5 mm in diameter bore (39 shown in FIG. 4A) in the S1 pedicle (P), the bore 39 axis being approximately normal to the coronal plane of L5-S1 disc space.

Figure 4A:
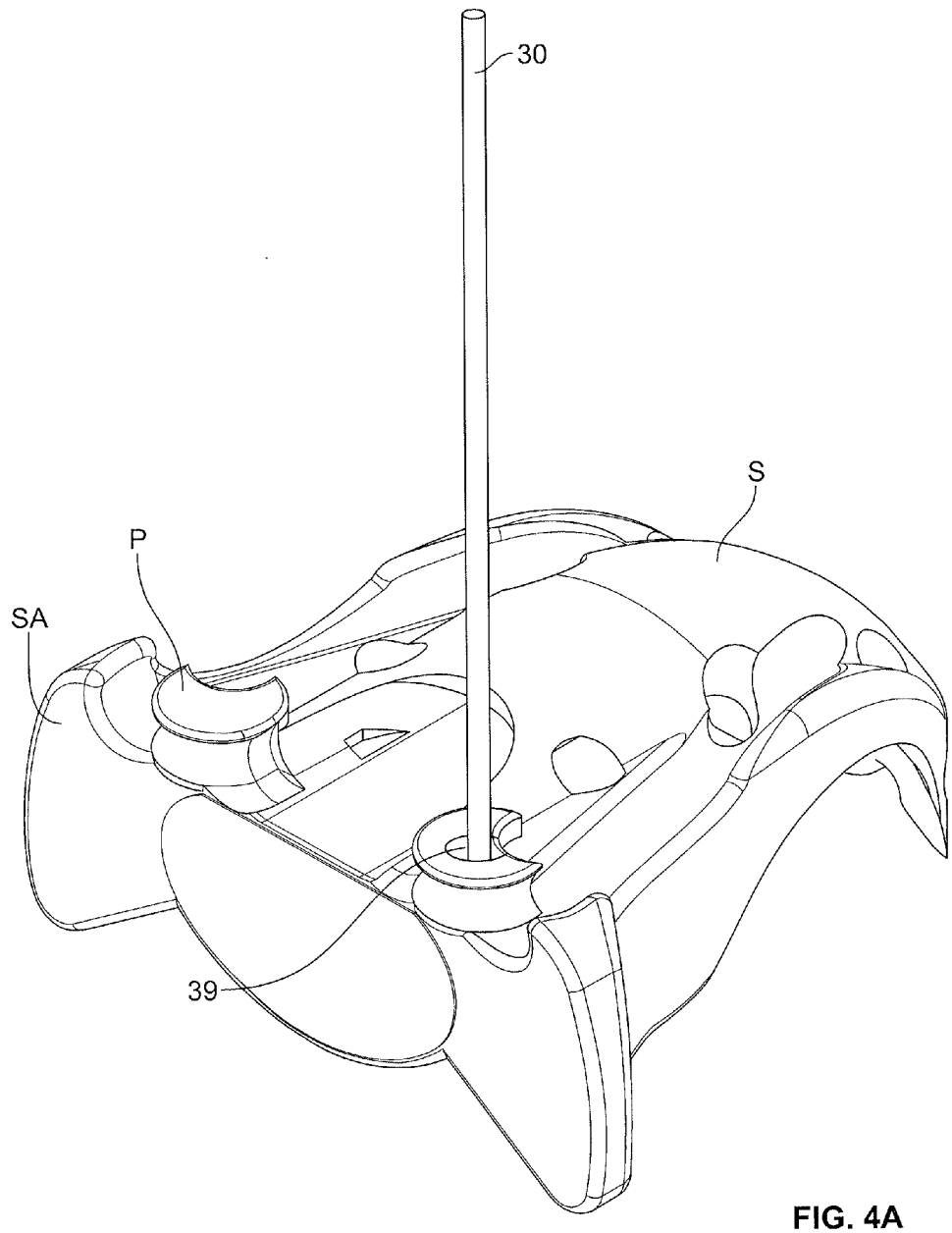
FIG. 4A is a simplified isometric view of the lumbosacral region of the spine where the cannulated reamer and the cannula have been removed leaving the guide pin inserted in the bored sacral pedicle according to various embodiments.
Figure 4B:
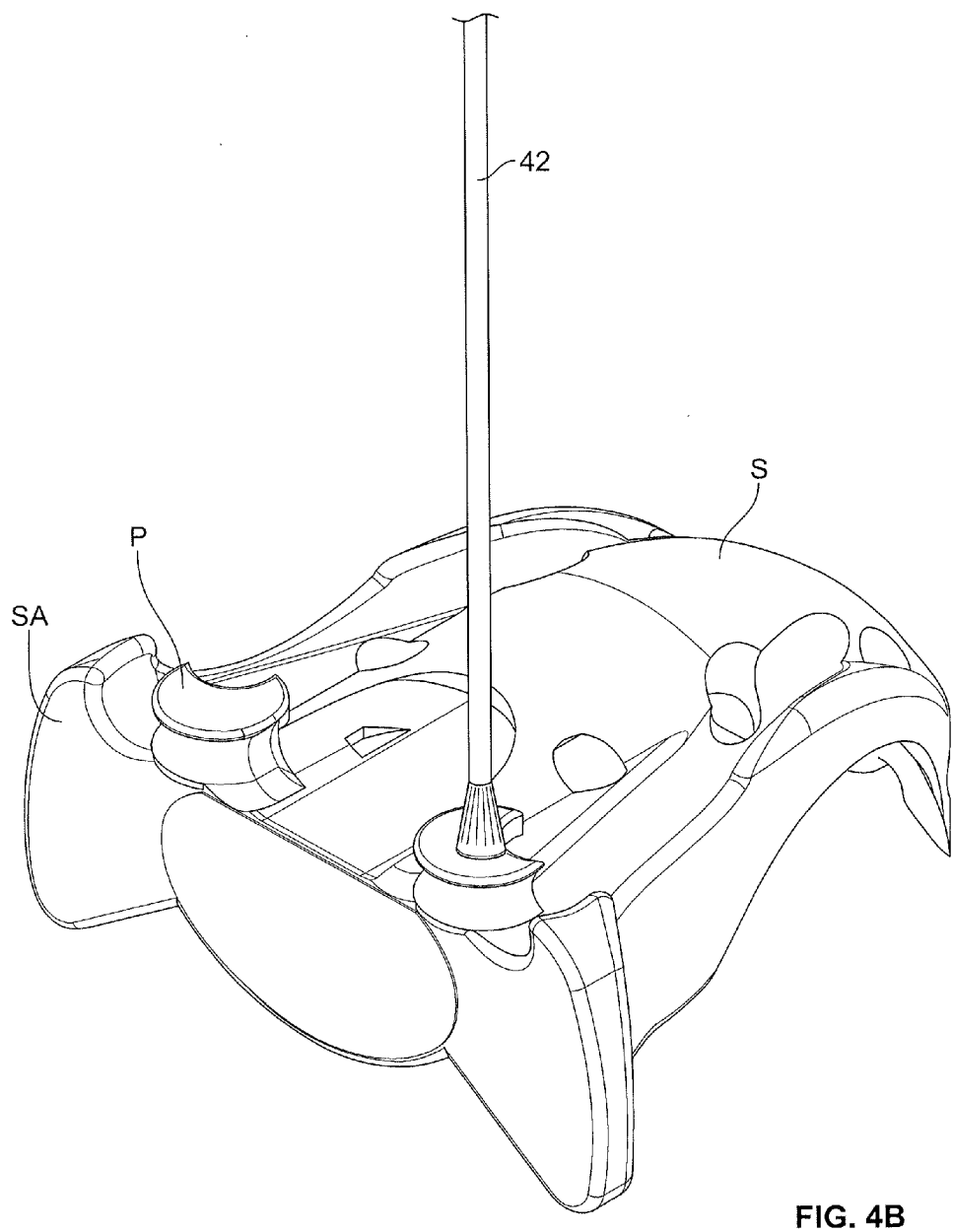
FIG. 4B is a simplified isometric view of the lumbosacral region of the spine shown in FIG. 4A further including a cannulated spot facer inserted over the guide pin, the spot facer being operatively advanced to the sacral pedicle to remove lumbosacral facet joint structures that might interfere with subsequent seating of a pedicle screw, according to various embodiments.

FIG. 4A is an isometric view of the L5-S1 region where the cannulated reamer 38 and the cannula 34 have been removed leaving the guide pin 30 inserted in the bored S1 pedicle (P) according to various embodiments. FIG. 4B is an isometric view of the L5-S1 region shown in FIG. 4A further including an end reamer or cannulated spot facer 42 inserted over the guide pin 30. In an embodiment, the spot facer 42 can be operatively advanced to the S1 pedicle (P), for example, to remove lumbosacral facet joint structures that might interfere with subsequent seating of a pedicle screw. The spot facer 42 can enlarge an upper section of the bore 39 formed in the S1 pedicle (P). In an embodiment the spot facer 42 has about a 12 mm diameter with a projected wall. In an embodiment the spot facer 42 forms a larger upper bore section to be occupied by a polyaxial or monoaxial pedicle receiving section, the section movably coupled or couplable to a sacral pedicle screw head and/or shank.

Alternatively, the support sleeve 32 can be left in place during preparation of the pedicle surface. Preparing the pedicle surface with an end reamer or "spot facer" while the support sleeve 32 remains in place can provide consistency and serve to control depth of penetration and ensure that the pedicle screw will sit on the surface of the pedicle entry site. The end reamer can have an internal bore of a corresponding length and diameter to that of the guide pin support sleeve 32 therein preventing the end reamer from penetrating too deeply into the pedicle entry surface. The support sleeve 32 can then be removed and a drill such as a cannulated drill with a stepped surface inserted over the guide pin 30 used to controllably achieve the prescribed depth. This sequence and arrangement provides a controlled and consistent drilling depth.

Figure 4C:
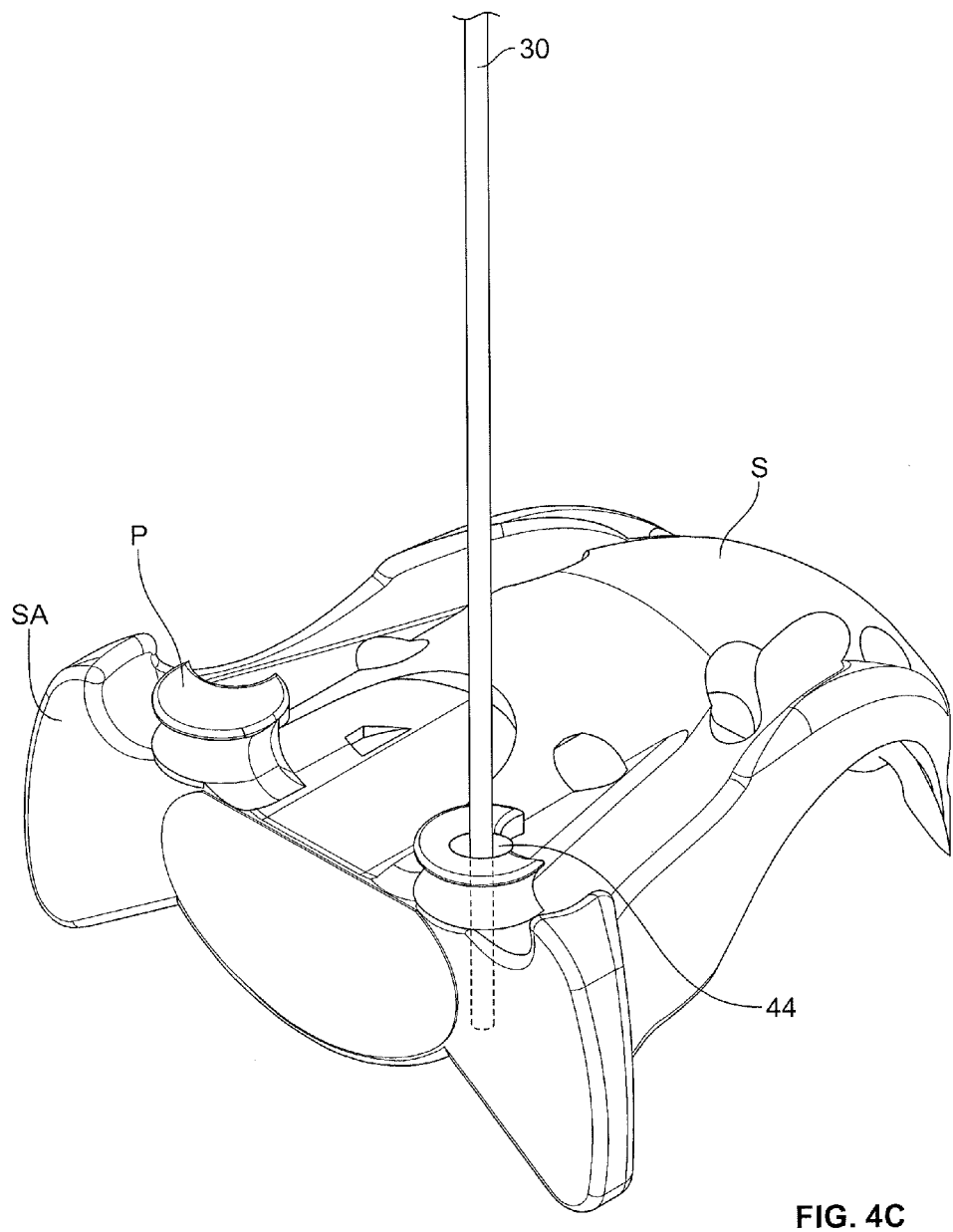
FIG. 4C is a simplified isometric view of the lumbosacral region of the spine where the cannulated spot facer has been removed leaving the guide pin inserted in the bored sacral pedicle according to various embodiments.
Figure 4D:
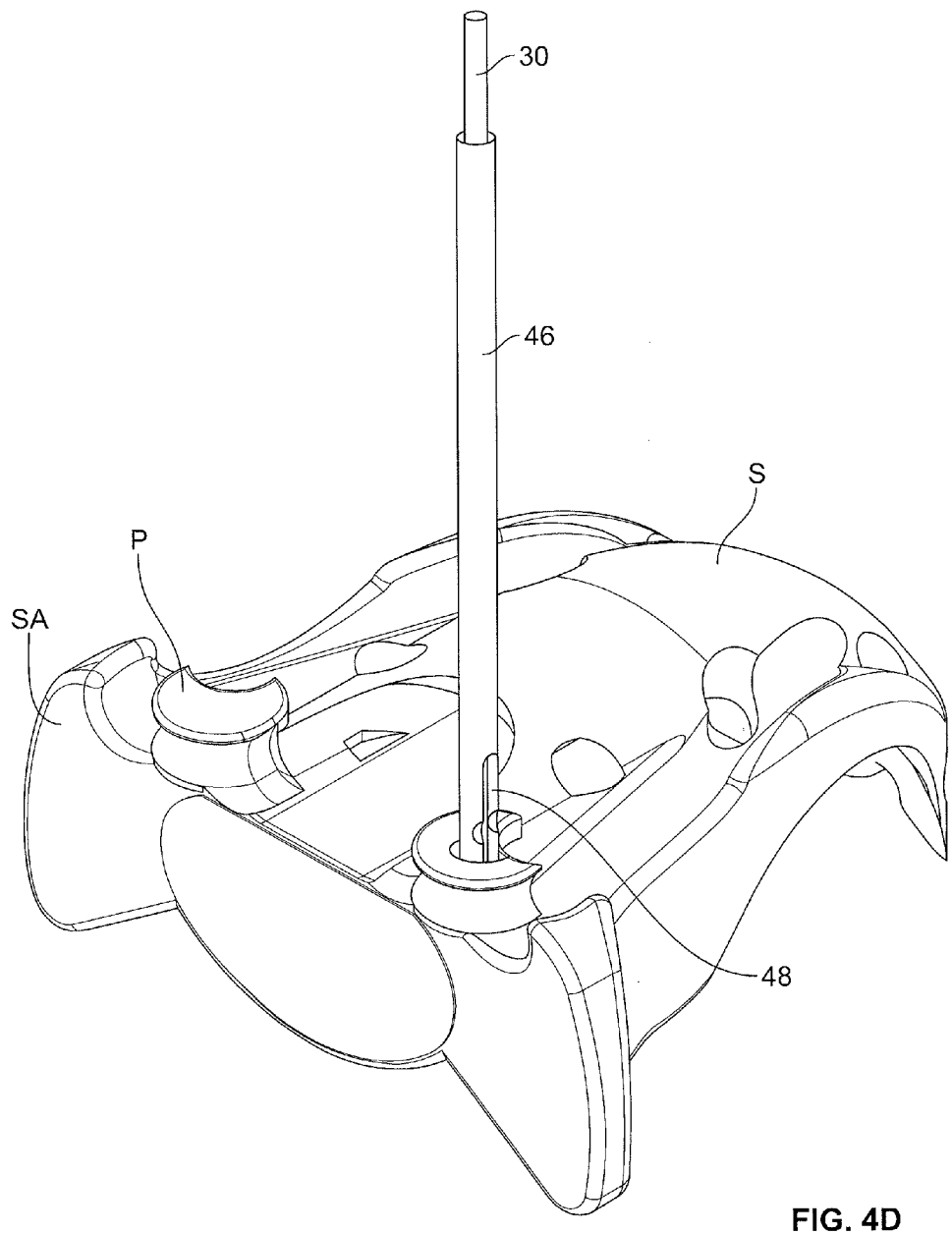
FIG. 4D is a simplified isometric view of the lumbosacral region of the spine shown in FIG. 4C further including a slotted cannula inserted over the guide pin, the cannula being advanced into the bore in the sacral pedicle according to various embodiments.

FIG. 4C is an isometric view of the L5-S1 region where the cannulated spot facer 42 has been removed leaving the guide pin 30 inserted in the bore 44 in the S1 pedicle (P) according to various embodiments. FIG. 4D is an isometric view of the L5-S1 region shown in FIG. 4C further including a cannula 46 inserted over the guide pin 30. The cannula 46 includes a slot 48 and is shown being advanced into the S1 pedicle (P) according to various embodiments.

Figure 5A:
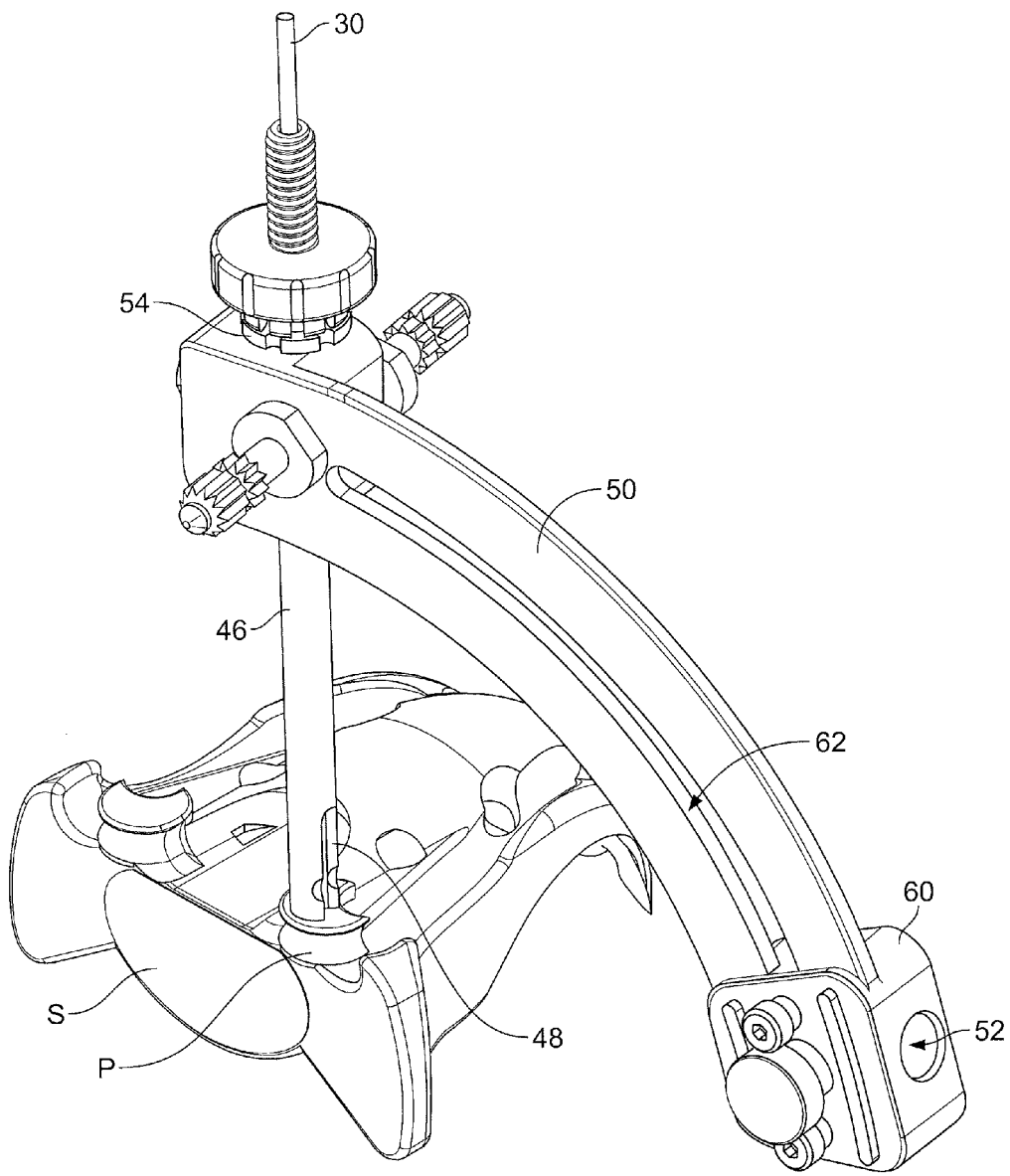
FIG. 5A is a simplified isometric view of the lumbosacral region of the spine shown in FIG. 4D further including a transiliac-transsacral channel alignment tool inserted over the cannula according to various embodiments.

FIG. 5A is an isometric view of the L5-S1 region shown in FIG. 4D further including a transiliac-transsacral channel alignment tool 50 inserted over the cannula 46 for the advancement of surgical tools through a transiliac-transsacral approach. The transiliac-transsacral channel pathway traverses the iliac ala or "wing", the sacroiliac joint, and an anatomic region of the sacrum, known as the sacral ala. The sacral ala is estimated to be 10-20 times the cross-sectional area of the S1 pedicles and has a substantially larger volume and cross-sectional area than the S1 pedicles. The anatomical structure of the sacral ala permits the introduction of larger surgical instruments than would otherwise be possible, via a pedicle access channel. The use of larger diameter instruments and devices without violating other anatomic structures or potentially injuring adjacent nerve roots increases the effectiveness and variety of applications this surgical approach provides. The larger volumetric and cross-sectional area of the sacral ala (compared to the S1 pedicles) facilitates a more predictable surgical targeting. This provides also for a greater potential for allowing surgical pathway convergence within the disc space. This affords more opportunity for instrument and device association from either side of the mid-sagittal plane. More complex surgical procedures are thereby permitted. For example, transfer of a device or material introduced through one access portal toward a device or material introduced form the contralateral access portal would be more easily facilitated. The method does not weaken, violate or remove bone from the S1 pedicle(s) in a manner that would potentially compromise S1 pedicle fixation. The sacral articular process of the L5-S1 facet joint is avoided and thus, the likelihood of violating, damaging or weakening those articulating structures or their osseous origins on either side of the midline and along the superior aspect of the S1 pedicles is reduced.

Figure 5B:
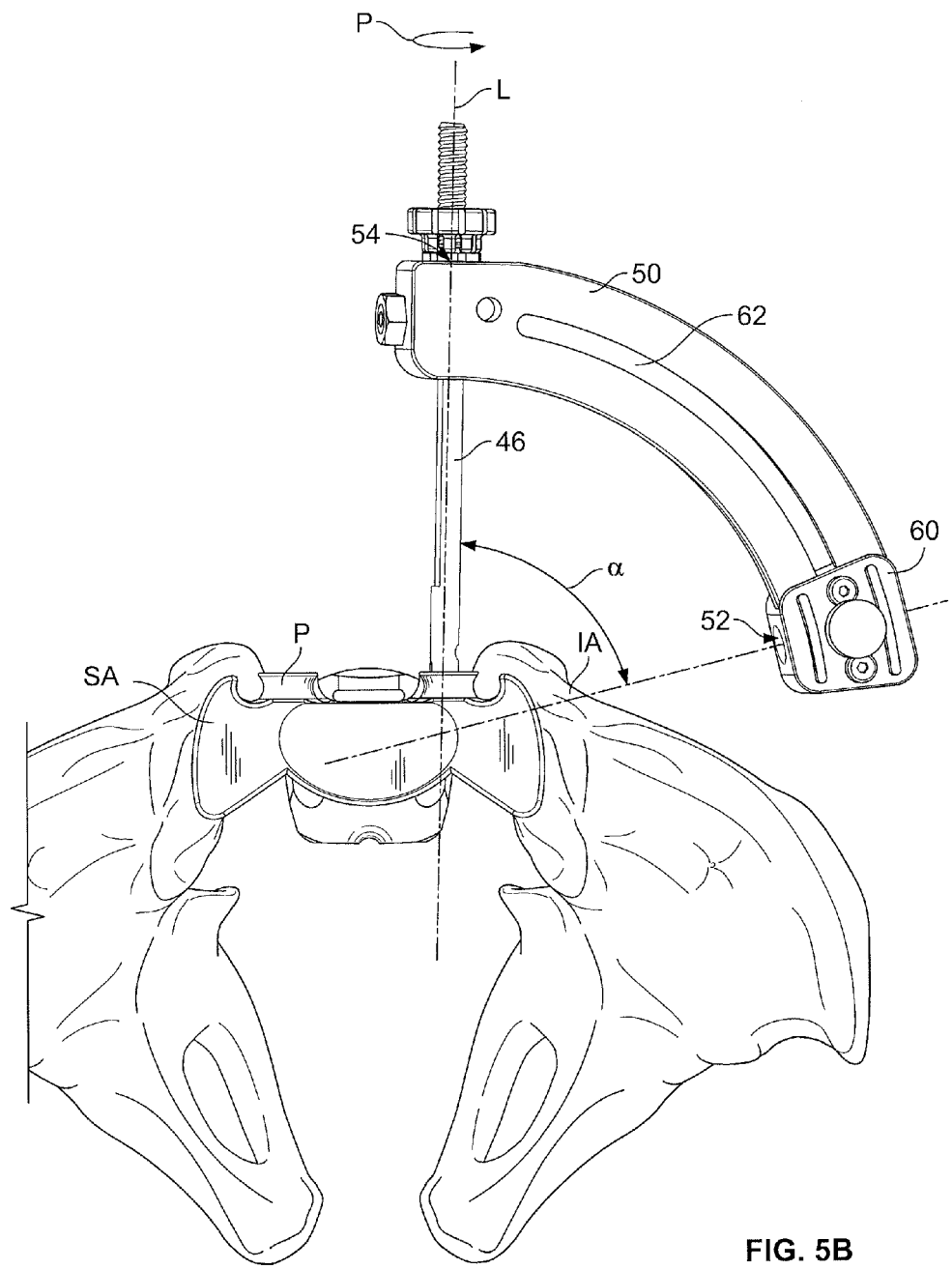
FIG. 5B is a simplified, transverse cephalad view of the lumbosacral region of the spine where the guide pin has been removed leaving the cannula inserted in the sacral pedicle bore and transiliac-transsacral channel alignment tool inserted over the cannula according to various embodiments.

Still with respect to FIG. 5A, the tool 50 includes a normal port 54 and an offset port 52. The normal port 54 can be sized to receive the guide pin 30 or slotted cannula 46. FIG. 5B is a transverse, cephalad view of the L5-S1 region where the guide pin 30 has been removed leaving the slotted cannula 46 inserted in the S1 pedicle (P) and a transiliac-transsacral channel alignment tool 50 inserted over the cannula 46 according to various embodiments. In one embodiment the normal port 54 of the alignment tool 50 can be sized to receive the slotted cannula 46.

The transiliac-transsacral channel to the L5-S1 disc space has the potential to approach the disc space and adjacent structures from a variety of anterior as well as a more posteriorly-located axis (sacral ala extends anterior and posterior to the S1 pedicles). The alignment tool 50 can be adjusted along its arch such that the offset port 52 is oriented to a variety of surgical axes to the normal port 54 as will be discussed in more detail below. The increased diversity of surgical axes affords the potential to access structures that would be otherwise inaccessible with the current methods known in the art. As shown in FIG. 5B, the alignment tool 50 can be aligned along an axis that approximates the plane of the L5-S1 disc space by rotating the alignment tool 50 around the longitudinal axis L of the cannula 46 in the normal port. This affects the caudal-cephalad angle of insertion of instrumentation through the offset port 52. Further, the angle α of the offset tool 50 can be changed by adjusting the position of the chassis 60 along groove 62. Set screws 37 or another fixing mechanism can fix the position of the chassis 60 within groove 62 at the desired angle α. In an embodiment the chassis 60 and its offset port 52 can be oriented at about a 50-100 degree angle relative to the longitudinal axis L of the normal port 54.

Figure 5C:
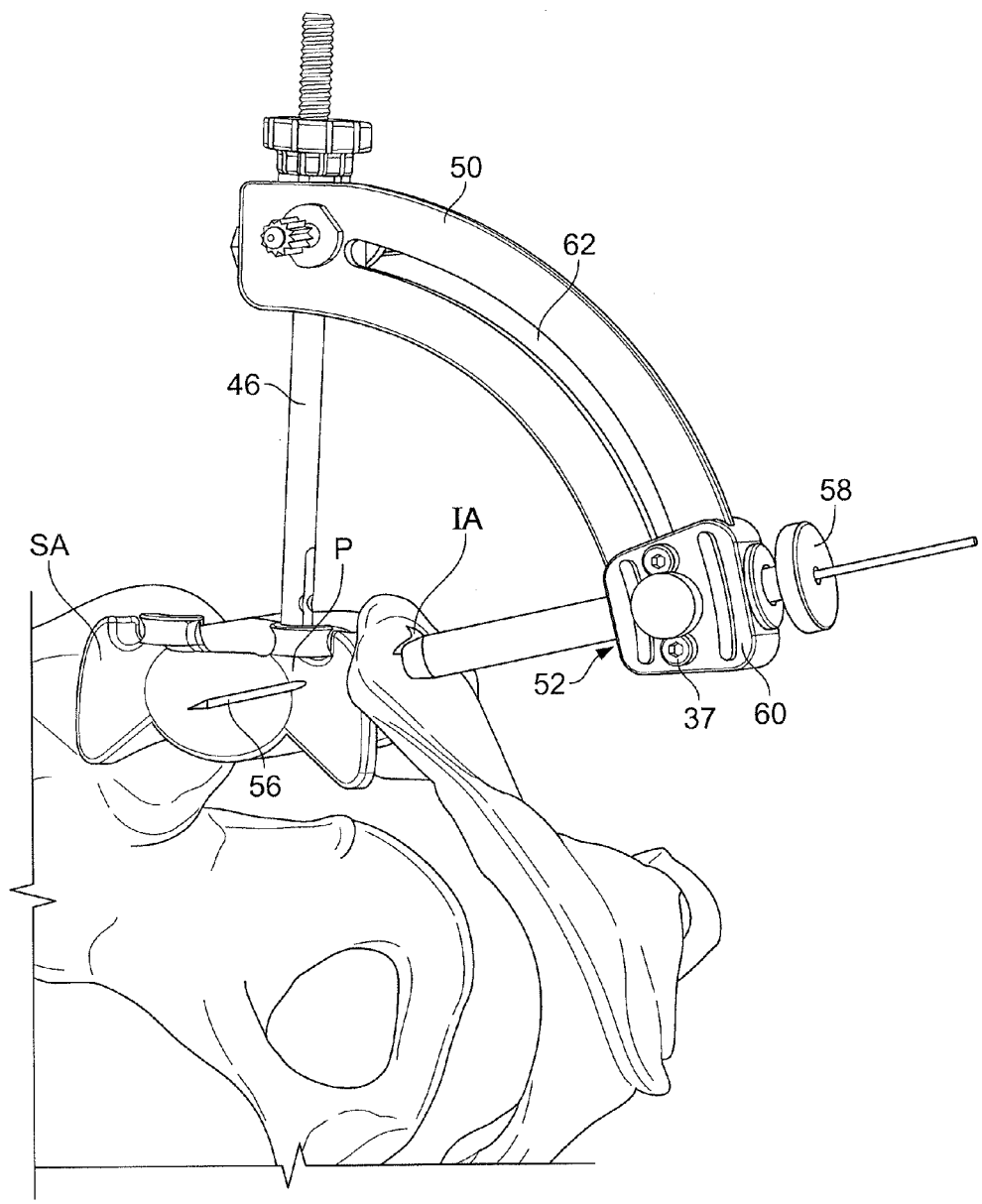
FIG. 5C is a simplified transverse cephalad view of the lumbosacral region of the spine shown in FIG. 5B further including a guide pin with support sleeve, the guide pin and support sleeve being inserted through the transiliac-transsacral channel alignment tool's offset guide port and the guide pin advanced from lateral to medial in the transverse plane and from caudal to cephalad in the sagittal plane, nearly parallel to the L5-S1 disc plane according to various embodiments.

FIG. 5C is a transverse cephalad view of the L5-S1 region shown in FIG. 5B further including an offset guide pin 56 with an offset support sleeve 58 inserted through the offset guide port 52 of the transiliac-transsacral channel alignment tool 50. In an embodiment, surgical navigation instrumentation can be used or one or more X-rays can be taken and reviewed to determine whether the offset guide pin 56 is proceeding along a desired pathway in the iliac ala (IA) and sacral ala (SA) prior to advancement into the disc space.

Figure 5D:
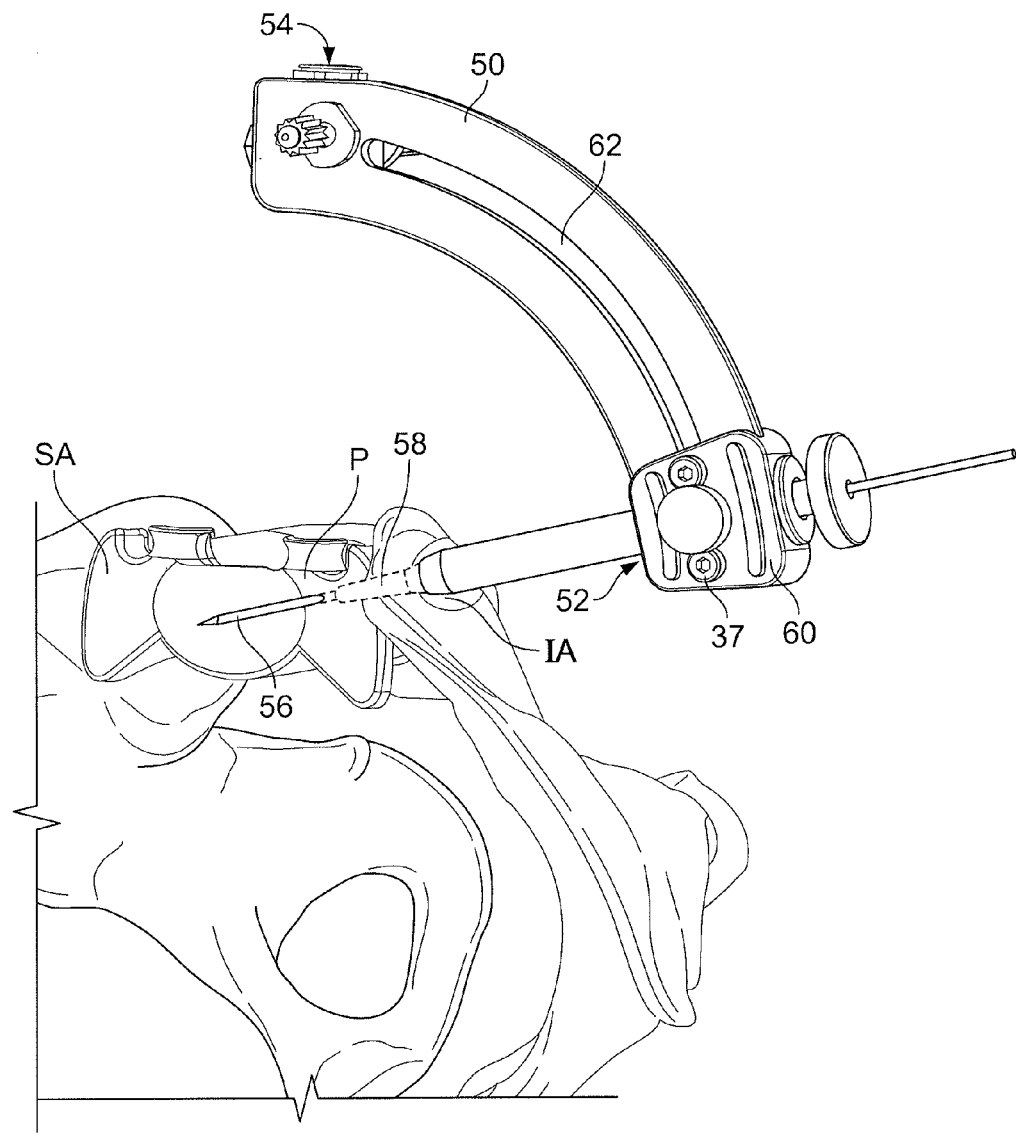
FIG. 5D is a simplified, transverse cephalad view of the lumbosacral region of the spine shown in FIG. 5C where the cannula in the transiliac-transsacral channel alignment tool's normal guide port has been removed leaving the guide pin and support sleeve inserted through the transiliac-transsacral channel alignment tool's offset guide port and the guide pin advanced at an angle nearly parallel to the L5-S1 disc plane according to various embodiments.

FIG. 5D is a transverse cephalad view of the L5-S1 region shown in FIG. 5C where the cannula 46 in the normal guide port 54 of the transiliac-transsacral channel alignment tool 50 has been removed. FIG. 5D shows an offset guide pin 56 and support sleeve 58 inserted through the offset guide port 52 of the transiliac-transsacral channel alignment tool 50 and the offset guide pin 56 advanced at the offset angle according to various embodiments.

Figure 6A:
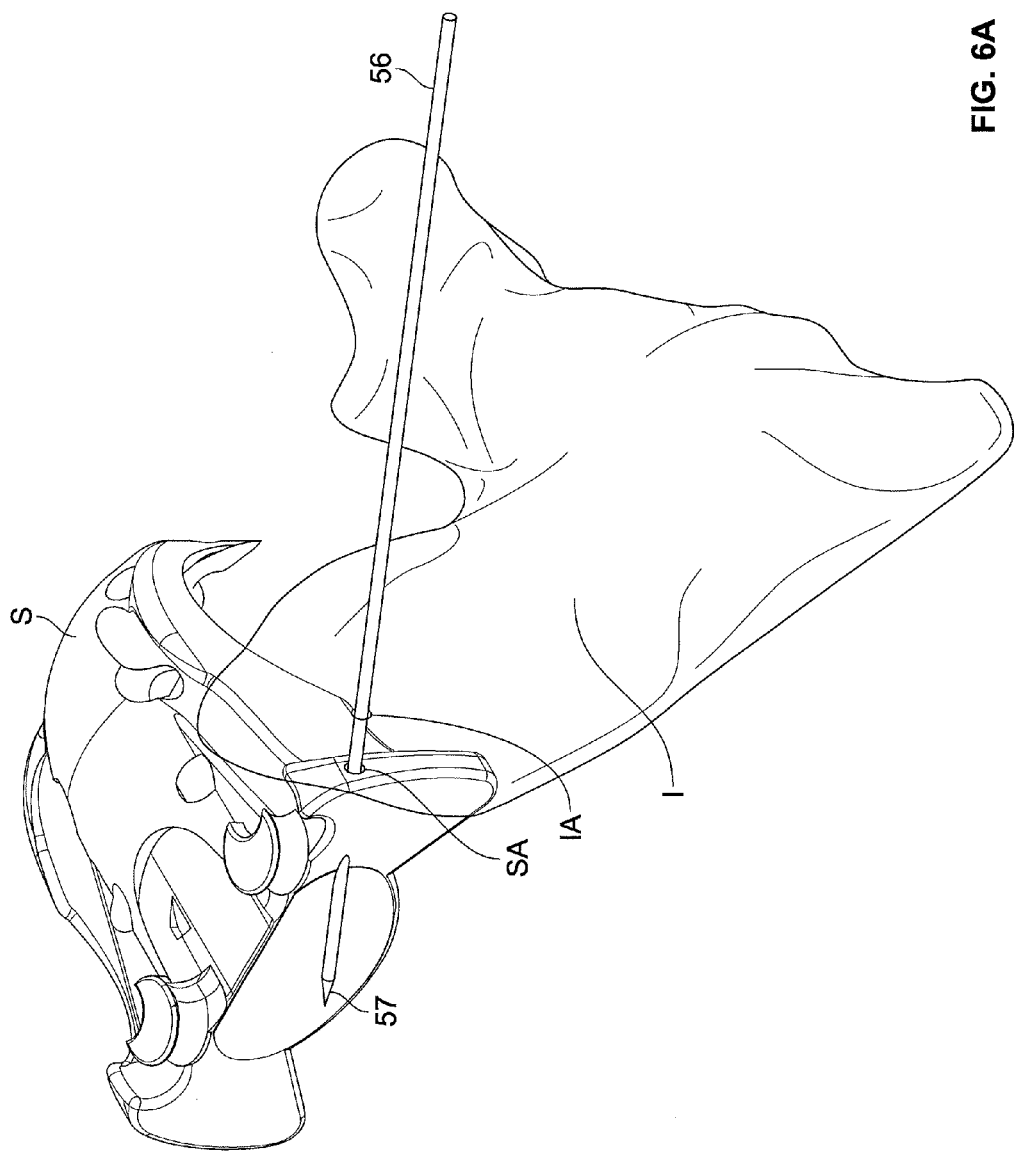
FIG. 6A is a simplified isometric view of the lumbosacral region of the spine shown in FIG. 5D where the support sleeve in the transiliac-transsacral channel alignment tool's offset guide port and the alignment tool have been removed leaving the guide pin inserted through a transiliac-transsacral channel into the disc space according to various embodiments.

FIG. 6A is an isometric view of the L5-S1 region shown in FIG. 5D where the offset support sleeve 58 and the alignment tool 50 have been removed leaving the offset guide pin 56 inserted through a transiliac-transsacral channel to the disc space according to various embodiments. The left ilium (I) is shown, but the right ilium is omitted for simplicity. As shown, the tip 57 of the guide pin 56 can project into the L5-S1 disc space. In an embodiment the transiliac-transsacral channel can be enlarged to enable different procedures to be performed in the disc space. The transiliac-transsacral channel can be positioned so that it is not adjacent or near any nerve pathways reducing the risk of nerve-related injuries due to a procedure being performed in the disc space. The surgical approach through the sacral ala allows for surgical access to the L5-S1 disc space with instrumentation in the S1 pedicle in place.

Figure 6B:
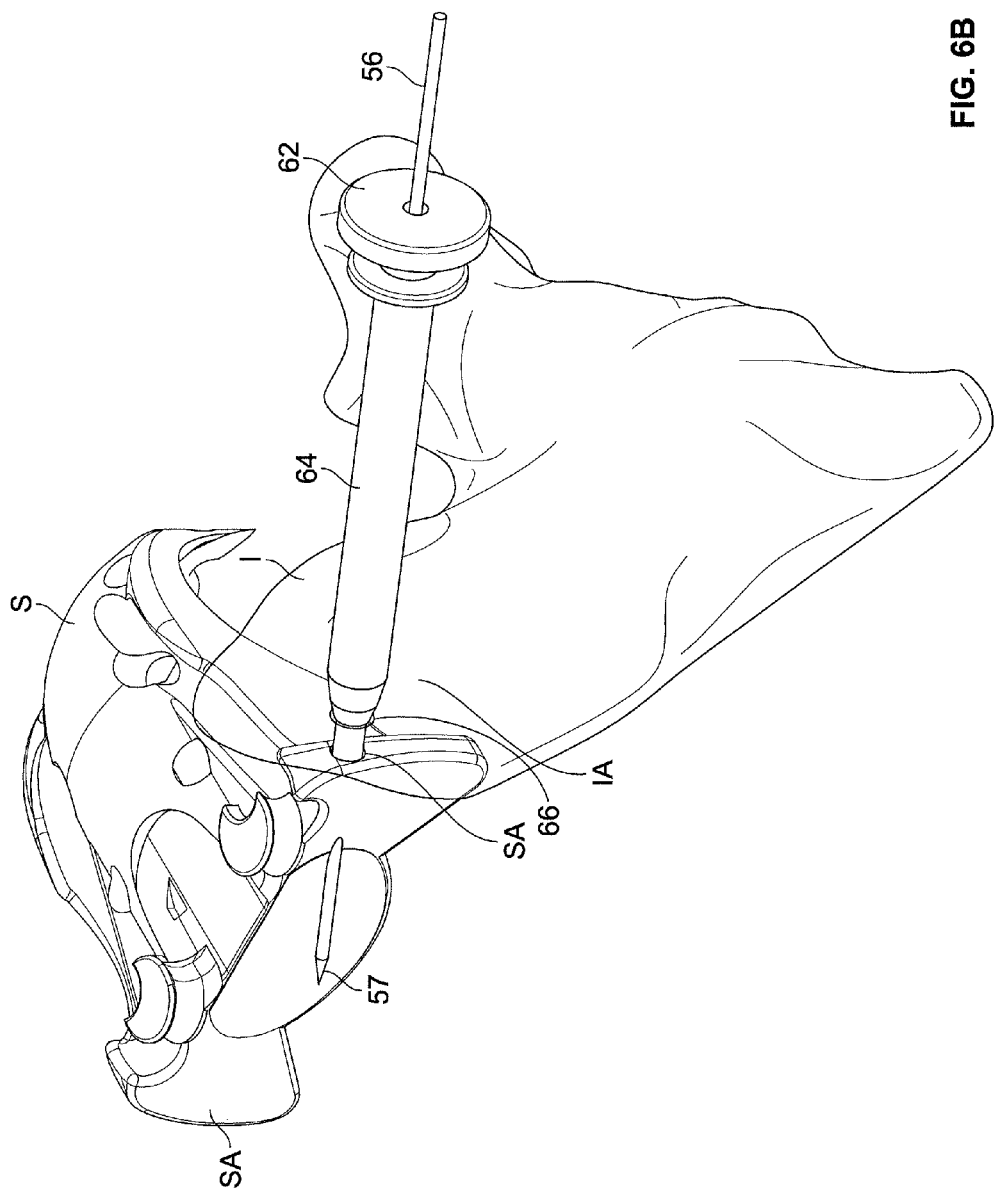
FIG. 6B is a simplified isometric view of the lumbosacral region of the spine shown in FIG. 6A further including a cannulated obturator within a cannula inserted over the guide pin.
Figure 6C:
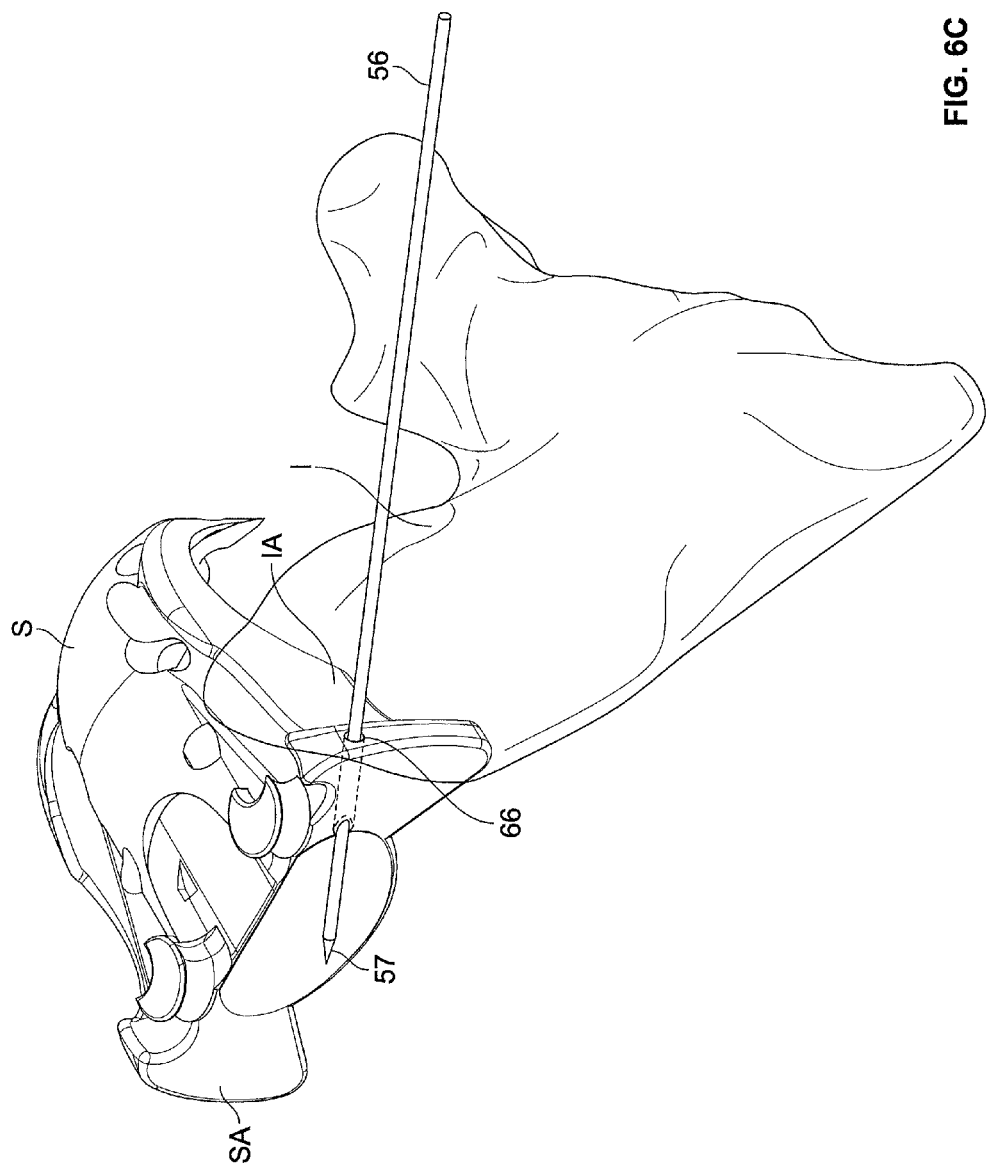
FIG. 6C is a simplified isometric view of the lumbosacral region of the spine shown in FIG. 6B where the cannulated obturator and the cannula have been removed leaving the guide pin inserted through the enlarged transiliac-transsacral channel into the disc space according to various embodiments.

FIG. 6B is an isometric view of the L5-S1 region shown in FIG. 6A further including a cannulated obturator 62 within a cannula 64 inserted over the offset guide pin 56. In an embodiment the obturator 62 can be operatively advanced into the disc space via the transiliac-transsacral channel and a reamer subsequently placed. The reamer can have a diameter ranging between 4 mm and 18 mm. In another embodiment, the reamer has a diameter of about 6.5 mm to form a channel 66 from the iliac ala (IA) and sacral ala (SA) to the disc space. FIG. 6C is an isometric view of the L5-S1 region shown in FIG. 6B where the cannulated obturator 62 and the cannula 64 have been removed leaving the guide pin 56 inserted through the transiliac-transsacral channel 66 to the disc space.

Figure 6D:
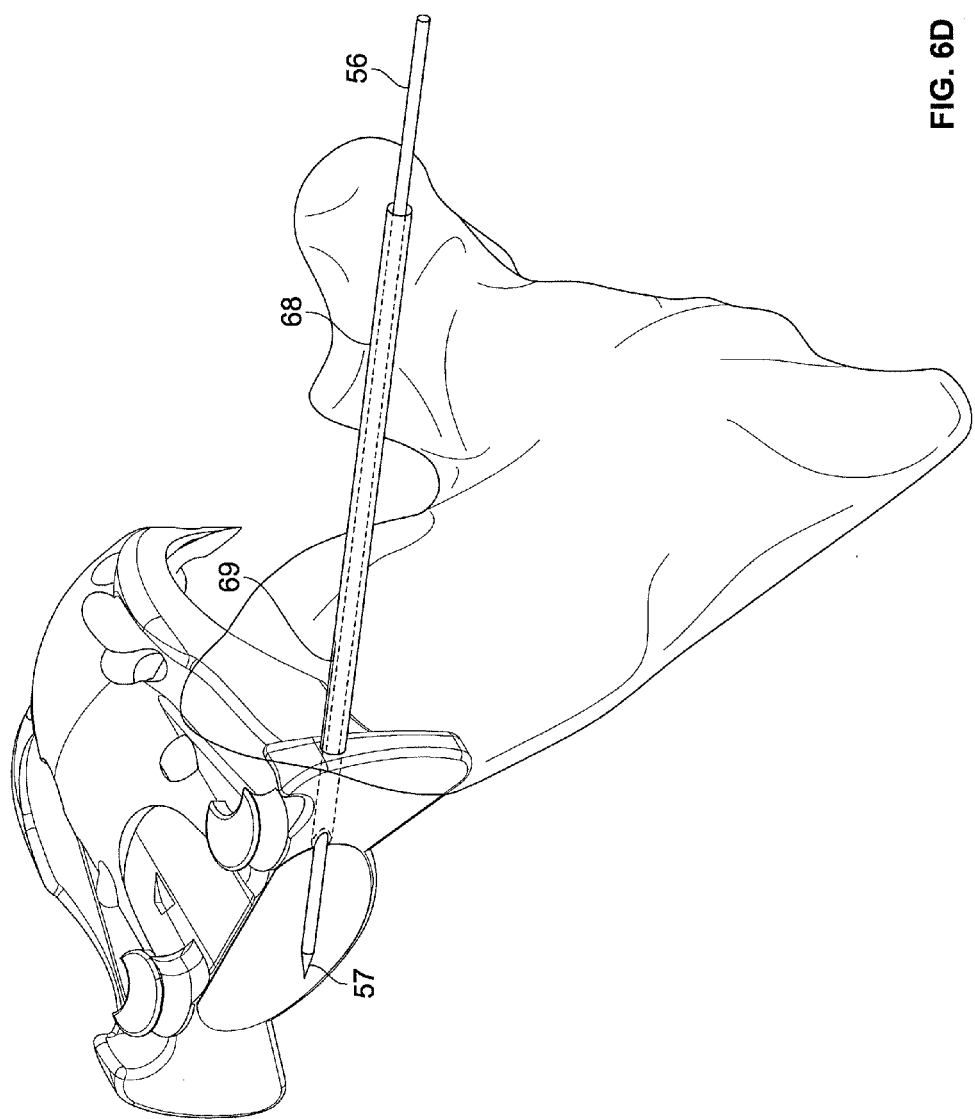
FIG. 6D is a simplified isometric view of the lumbosacral region of the spine shown in FIG. 6C further including a cannula inserted over the guide pin, the cannula being advanced into disc space via the transiliac-transsacral channel according to various embodiments.
Figure 6E:
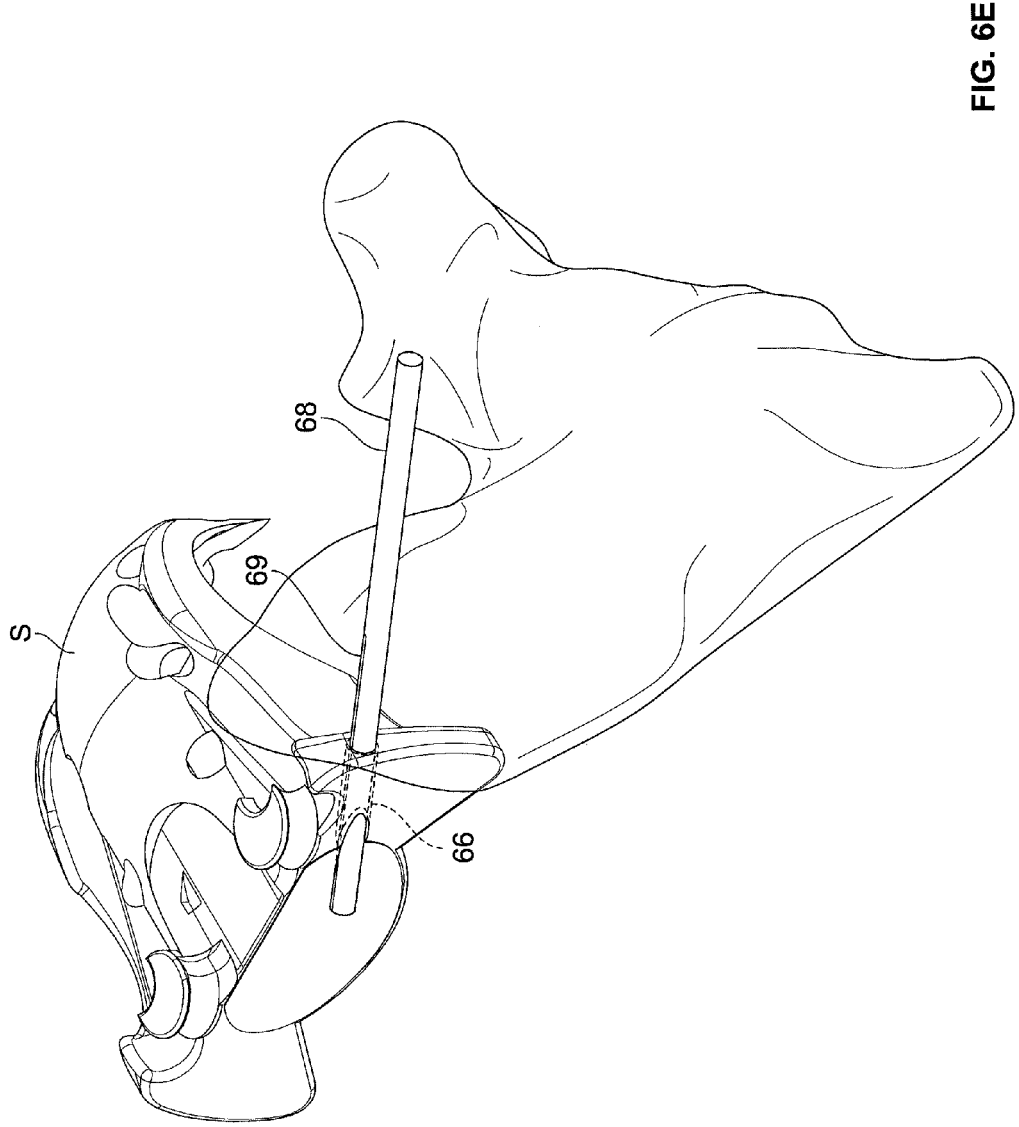
FIG. 6E is a simplified isometric view of the lumbosacral region of the spine shown in FIG. 6B where the guide pin has been removed leaving the working channel cannula in the enlarged transiliac-transsacral channel to the disc space according to various embodiments.

In FIG. 6D, an obturator (cannulated if the guide pin is left in place) and thin walled cannula 68 are introduced into the transiliac-transsacral ala channel, and into the L5-S1 disc space. The obturator (and guide pin if previously left within the channel) is removed, and a protected direct path from the outside of the patient's body to the disc space of L5-S1 (potentially bilaterally) is afforded.

Various tools and instruments can be employed via the cannula 68 to perform procedures within the L5-S1 disc space using at least a portion of the intraosseous channel. For example, it might be desirable to use the transiliac-transsacral approach to remove disc material, osteophytes or other structures that might be impinging on the nerve root(s), including herniated or prolapsed disc material. Other procedures that can be performed through a portion of the intraosseous channel in addition to discectomy, include functional placement devices such as nucleoplasty or arthroplasty devices, endplate "decortication" instruments, annular closure or repair instruments and implants, fusion instrumentation and implants or intervertebral disc arthrodesis devices, fracture reduction devices, bone cyst therapy, intervertebral distraction devices, spacers or cages. Implantation of therapeutic materials such as bone growth materials, nuclear replacement material, bone granules, powdered material, and bone grafting material (autogenous, allogeneic, xenograph, or synthetic) as well as any osteoconductive and/or proliferative material, are also considered herein. More specifically, therapeutic bone growth materials such as osteogenic proteins or growth factors including osteoprogenic factor 1, BMP-7, and bone morphogenetic proteins such as BMP-2.

As mentioned above, the alignment tool 50 can be used to create transiliac-transsacral channels at a variety of angles relative to the coronal, transverse, and sagittal planes relative to the axial plane of the disc space via the iliac and sacral alae (IA, SA). In an embodiment, the angle subtended by the axis of the transiliac-transsacral ala access channel relative to the axial plane of the disc space is between about 5 and 50 degrees. In another embodiment, the transiliac-transsacral ala access channel aligns generally parallel to a coronal plane of the L5-S1 disc space. In another embodiment, the transiliac-transsacral ala access channel aligns generally parallel to a coronal plane of the L5-S1 disc space and at an angle that is between about 5 and 40 degrees relative to the axial plane of the L5-S1 disc. In another embodiment, the transiliac-transsacral ala access channel aligns generally parallel to a coronal plane of the L5-S1 disc space and at an angle that is between about 5 and 20 degrees relative to the axial plane of the L5-S1 disc. In another embodiment, the transiliac-transsacral ala access channel aligns generally parallel to a coronal plane of the L5-S1 disc space and at an angle that is generally parallel to the axial plane of the L5-S1 disc.

The transiliac-transsacral intraosseous channel can terminate in the disc space through the posterior aspect of the superior endplate of the L5 vertebra. Alternatively, the transiliac-transsacral intraosseous channel can terminate adjacent to the superior aspect of the S1 pedicle or at or near the pedicle-vertebral body juncture, and entering the neuroforamina. This surgical pathway can be used for disc or bone resection of adjacent structures for the purpose of decompression of adjacent nerve roots.

It should be appreciated that procedures can be performed within the disc space and into the L5 vertebra through the transiliac-transsacral channels unilaterally or bilaterally. For example, an offset transiliac-transsacral working channel can be similarly placed contra-laterally. Various surgical interventions can be performed through one, either or both of these working or access channels, including disc excision, endplate preparation, implant insertion and positioning, distraction, insertion of lumbosacral transfixation constructs or other fusion constructs, bone dowels, bone grown materials, allograft material, kyphoplasty, and other vertebra height restoration or modification procedures etc. according to various embodiments. After performing one or more procedures via the transiliac-transsacral working channel(s), it can be desirable to access the normal S1 pedicle bore 44 to perform one or more procedures via the normal S1 pedicle channel 45. For example, a pedicle screw can be inserted through the normal S1 pedicle entry for subsequent pedicle screw fixation.

Figure 7A:
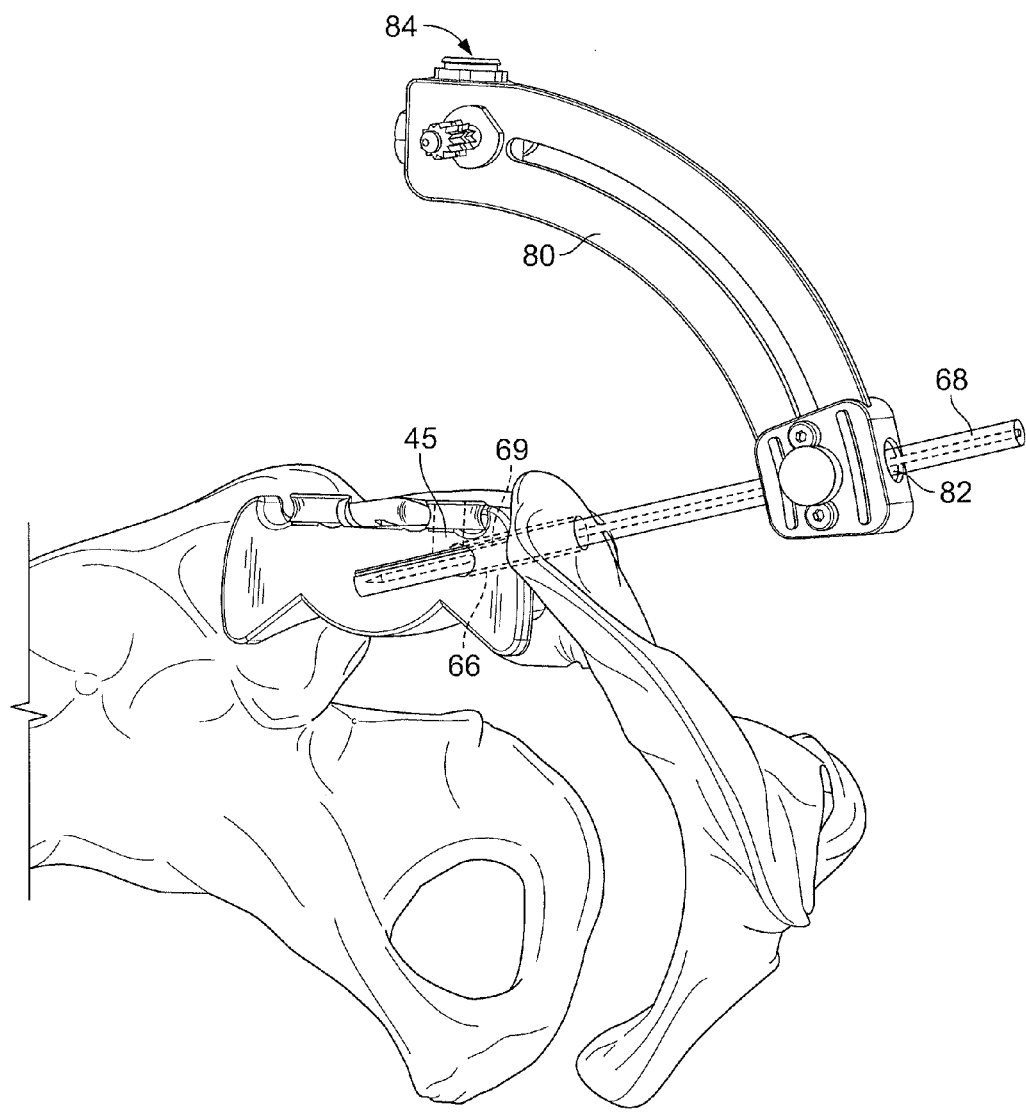
FIG. 7A is a simplified isometric view of the lumbosacral region of the spine shown in FIG. 6D including a reverse sacral pedicle alignment tool inserted over the working channel cannula according to various embodiments.
Figure 7B:
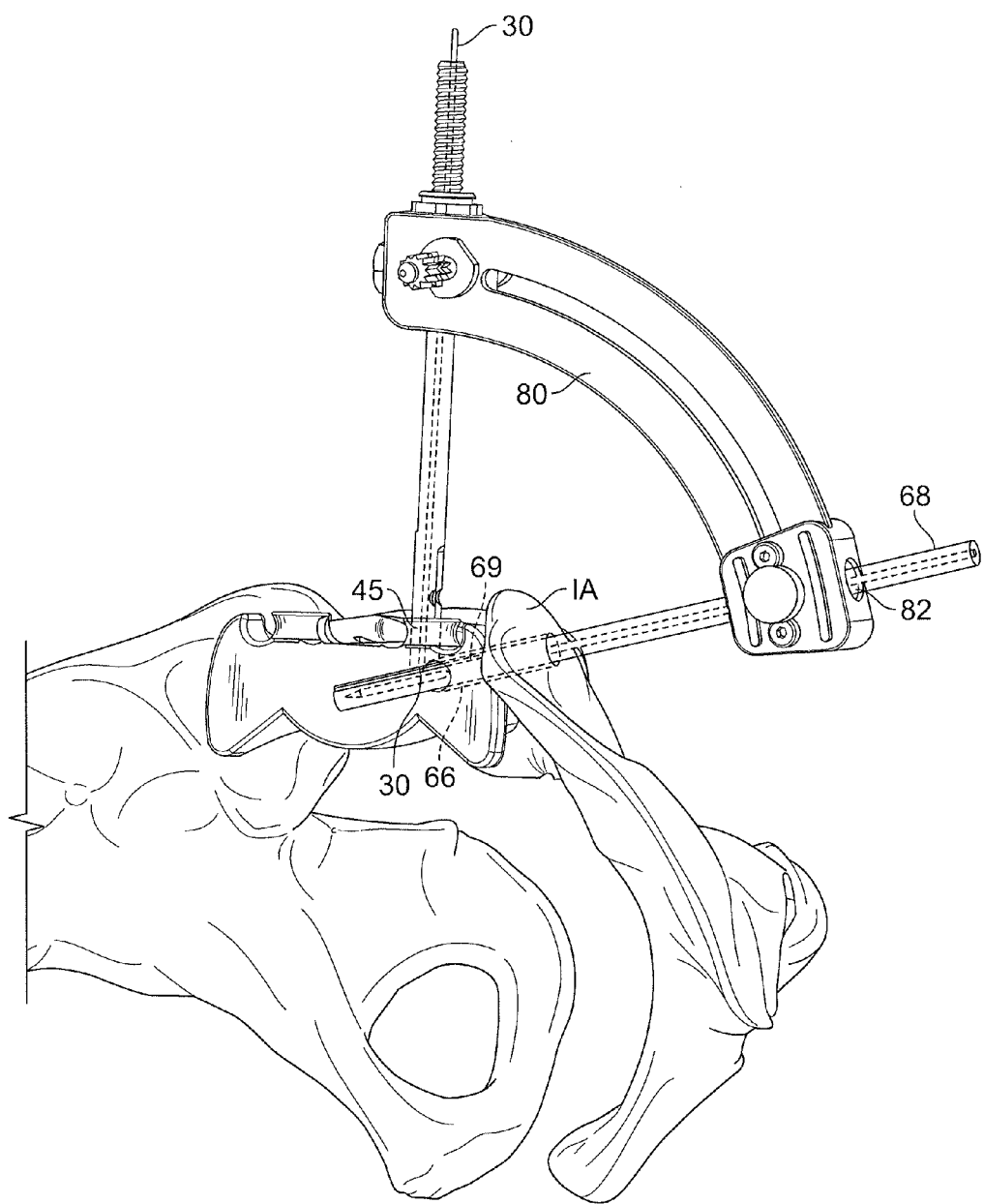
FIG. 7B is a simplified isometric view of the lumbosacral region of the spine shown in FIG. 7A including the guide pin inserted in the reverse alignment tool's normal port and through the cannula's slot according to various embodiments.

FIG. 7A is an isometric view of the lumbosacral region shown in FIG. 6D including an alignment tool 80 inserted over the offset slotted 69 cannula 68 according to various embodiments. The tool 80 includes an offset guide port 82 and a normal guide port 84. The offset guide port 82 can be sized to fit the offset cannula 68. FIG. 7B is a simplified isometric view of the lumbosacral region shown in FIG. 7A including the guide pin 30 inserted in the normal guide port of the alignment tool 80. This can facilitate accurate repositioning of a guide pin into the previously formed sacral pedicle bore and thus allow for insertion of a cannulated pedicle screw. Alternatively, the guide can be used to directly place a pedicle screw without the aid of a guide pin.

While this specification contains many specifics, these should not be construed as limitations on the scope of the claims or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features can be described above as acting in certain combinations and even initially claimed as such, one or more features from a claimed combination can in some cases be excised from the combination, and the claimed combination can be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method comprising:
    accessing a lumbosacral joint of a patient by percutaneously inserting bone penetration instrumentation using one or more instrument insertions unilaterally or bilaterally through an iliac ala, sacroiliac joint, and sacral ala to a region of a L5-S1 disc space forming a bony pathway traversing through the iliac ala, sacroiliac joint, and sacral ala to enter the L5-S1 disc space,
    wherein the bony pathway extends along an axis that enters the L5-S1 disc space from a posterolateral to lateral position towards a anteromedial to medial position.

2. The method of claim 1, wherein the bony pathway approaches the L5-S1 disc space at an angle that is between 5 and 40 degrees relative to a coronal plane of the L5-S1 disc.

3. The method of claim 1, wherein the bony pathway approaches the L5-S1 disc space at an angle that is between 5 and 20 degrees relative to a coronal plane of the L5-S1 disc.

4. The method of claim 1, wherein the bony pathway approaches the L5-S1 disc space at an angle that is generally parallel to an axial plane of the L5-S1 disc.

5. The method of claim 1, further comprising percutaneously placing a guide instrument in a first sacral pedicle, wherein the guide instrument is configured to guide, stabilize and provide anatomic reference for subsequent insertion of the bone penetration instrumentation.

6. The method of claim 5, wherein the guide instrument placed in the first sacral pedicle has a longitudinal axis that extends within an axial plane generally caudal to and parallel with an axial plane bisecting the L5-S1 disc space, the guide instrument extending from a generally posterior to posterior-lateral aspect of the first sacral pedicle to a generally anterior or anterior-medial aspect of the first sacral pedicle.

7. The method of claim 6, further comprising attaching to the guide instrument placed in the first sacral pedicle a curvilinear frame comprising a port having a port channel axis adjustably offset at an angle from the longitudinal axis of the guide instrument.

8. The method of claim 7, wherein the curvilinear frame provides an arcuate track along which the port provides a directed surgical path intersecting the longitudinal axis of the guide instrument at a location anterior to the sacral pedicle.

9. The method of claim 8, further comprising adjusting the port along the curvilinear frame such that the angle of the port channel axis relative to the longitudinal axis of the guide instrument is between 50 and 100 degrees.

10. The method of claim 8, wherein inserting the bone penetration instrumentation using one or more instrument insertions comprises inserting the bone penetration instrumentation through the port to direct a distal end of the bone penetration instrumentation to contact the iliac ala before forming the bony pathway traversing through the iliac ala, the sacroiliac joint, and the sacral ala.

11. The method of claim 1, further comprising inserting instrumentation through the bony pathway and performing disc excision in the L5-S1 disc space.

12. The method of claim 1, wherein the bone penetration instrumentation extends through the L5-S1 disc space to contact the vertebral body of L5 vertebra.

13. The method of claim 12, further comprising inserting an instrument through the bony pathway and performing an endplate procedure of the contacted vertebral body of the L5 vertebra.

14. The method of claim 1, further comprising inserting a lumbosacral transfixation construct through the bony pathway formed using the bone penetration instrumentation.

15. The method of claim 1, further comprising performing an intervention selected from the group consisting of intervertebral fixation, intervertebral distraction, intervertebral fusion, disc excision, arthroplasty and nucleoplasty through the bony pathway formed using the bone penetration instrumentation.

16. The method of claim 1, further comprising percutaneously inserting the bone penetration instrumentation using one or more instrument insertions through a contra-lateral iliac ala, sacroiliac joint, and sacral ala to the region of the L5-S1 disc space forming a contra-lateral bony pathway traversing through the contra-lateral iliac ala, sacroiliac joint, and sacral ala.

17. The method of claim 16, wherein the contra-lateral bony pathway provides bilateral access to the region of the L5-S1 disc space.

* * * * *